United States Patent
Guo

(10) Patent No.: US 11,512,344 B2
(45) Date of Patent: Nov. 29, 2022

(54) CONSECUTIVE HYBRIDIZATION FOR MULTIPLEXED ANALYSIS OF BIOLOGICAL SAMPLES

(71) Applicant: ARIZONA BOARD OF REGENTS ON BEHALF OF ARIZONA STATE UNIVERSITY, Scottsdale, AZ (US)

(72) Inventor: Jia Guo, Tempe, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 142 days.

(21) Appl. No.: 16/300,148

(22) PCT Filed: Apr. 25, 2017

(86) PCT No.: PCT/US2017/029271
§ 371 (c)(1),
(2) Date: Nov. 9, 2018

(87) PCT Pub. No.: WO2017/196527
PCT Pub. Date: Nov. 16, 2017

(65) Prior Publication Data
US 2019/0144932 A1    May 16, 2019

Related U.S. Application Data

(60) Provisional application No. 62/334,047, filed on May 10, 2016.

(51) Int. Cl.
*C12Q 1/68* (2018.01)
*C12Q 1/6841* (2018.01)
(Continued)

(52) U.S. Cl.
CPC ......... *C12Q 1/6841* (2013.01); *C12Q 1/6825* (2013.01); *G01N 21/64* (2013.01); *G01N 21/6428* (2013.01); *G01N 2021/6439* (2013.01)

(58) Field of Classification Search
USPC ......... 435/6.1, 6.11, 91.1, 183; 436/94, 501; 536/23.1, 24.3, 24.33, 25.3, 25.32
See application file for complete search history.

(56) References Cited

U.S. PATENT DOCUMENTS 6,066,459 A    5/2000  Garini
9,933,431 B2   4/2018  Guo
(Continued)

OTHER PUBLICATIONS

International Search Report and Written Opinion for International Patent Application No. PCT/US2017/029271 dated Jul. 20, 2017.
(Continued)

*Primary Examiner* — Frank W Lu
(74) *Attorney, Agent, or Firm* — Quarles & Brady, LLP

(57) ABSTRACT

Provided herein are high-throughput, high-quality methods of consecutive in situ hybridization for analysis of the genome and/or transcriptome in an individual cell with single-molecule sensitivity. In particular, provided herein are methods comprising visualizing individual genomic loci or transcripts as single detectable signals (e.g., fluorescent spots) which remain in place during consecutive hybridization. In each cycle of consecutive hybridization, detectably labeled probes hybridize to the probe used in the previous cycle, and also introduce the binding sites for the probe of the following cycle. Through consecutive cycles of probe hybridization, imaging, and signal removal, different genomic loci or RNA species can be identified by unique detectable signal profiles (e.g., fluorescent spots with unique color sequences). The number of varied color sequences
(Continued)

increases exponentially with the number of hybridization cycles, which enables the genome or transcriptome-wide analysis.

7 Claims, 9 Drawing Sheets

Specification includes a Sequence Listing.

(51) Int. Cl.
*G01N 21/64* (2006.01)
*C12Q 1/6825* (2018.01)

(56) References Cited

U.S. PATENT DOCUMENTS

2006/0228733 A1   10/2006   Pierce
2015/0267251 A1    9/2015   Cai et al.
2016/0054308 A1    2/2016   Guo

OTHER PUBLICATIONS (Huang, J et al.) Fluorescence resonance energy transfer-based hybridization chain reaction for in situ visualization of tumor-related mRNA. Chemical Science. Feb. 25, 2016, vol. 7; pp. 3829-3835; p. 3830, 1st col. 2nd paragraph; scheme 1; DOI: 10.1039/c6sc00377j.
Barker N et al. (2012) Lgr5+ve Stem/Progenitor Cells Contribute to Nephron Formation during Kidney Development. Cell Rep 2:540-552.
Bayani et al. "Multi-color FISH techniques." Current protocols in cell biology (2004). 22.5.1-22.5.25.
Beliveau BJ et al. (2012) Versatile design and synthesis platform for visualizing genomes with Oligopaint FISH Natl Acad Sci U S A 109:21301-6.
Chen KH, et al. (2015) Spatially resolved, highly multiplexed RNA profiling in single cells. Science 1363:1360-1363.
Crosetto N, et al. (2014) Spatially resolved transcriptomics and beyond. Nat Rev Genet 16:57-66.
Dalerba P et al. (2011) Single-cell dissection of transcriptional heterogeneity in human colon tumors. Nat Biotechnol 29:1120-7.
Danilova, T.V., et al. "Integrated cytogenetic map of mitotic metaphase chromosome 9 of maize: resolution, sensitivity, and banding paint development." Chromosoma 117.4 (2008): 345-356.
Femino A M,et al (1998) Visualization of single RNA transcripts in situ. Science 280:585-590.
Fransz, P, et al. "Interphase chromosomes in Arabidopsis are organized as well defined chromocenters from which euchromatin loops emanate." Proceedings of the National Academy of Sciences 99.22 (2002): 14584-14589.
Gerdes, M. J., et al. "Highly multiplexed single-cell analysis of formalin-fixed, paraffin-embedded cancer tissue." Proceedings of the National Academy of Sciences 110.29 (2013): 11982-11987.
Guo W et al. (2012) Slug and Sox9 Cooperatively Determine the Mammary Stem Cell State. Cell 148:1015-1028.
Hoheisel JD (2006) Microarray technology: beyond transcript profiling and genotype analysis. Nat Rev Genet 7:200-10.
Tzkovitz S et al. (2012) Single-molecule transcript counting of stem-cell markers in the mouse intestine. Nat Cell Biol 14:106-14.
Ke R et al. (2013) In situ sequencing for RNA analysis in preserved tissue and cells. Nat Methods 10:857-60.
Lee JH et al. (2014) Highly multiplexed subcellular RNA sequencing in situ. Science 343:1360-3.
Lee, JH et al. (2015) Fluorescent in situ sequencing (FISSEQ) of RNA for gene expression profiling in intact cells and tissues. Nat Protoc 10:442-58.
Levesque MJ, et al. (2013) Single-chromosome transcriptional profiling reveals chromosomal gene expression regulation. Nat Methods 10:246-8.
Levsky JM, et al. (2002) Single-cell gene expression profiling. Science 297:836-40.
Lin, J.-R., et al. "Highly multiplexed imaging of single cells using a high-throughput cyclic immunofluorescence method." Nature communications 6 (2015): 8390.
Lubeck E, et al. (2012) Single-cell systems biology by super-resolution imaging and combinatorial labeling. Nat Methods 9:743-8.
Lubeck E, et al. (2014) Single-cell in situ RNA profiling by sequential hybridization. Nat Methods 11:360-361.
Lyubimova A et al. (2013) Single-molecule mRNA detection and counting in mammalian tissue. Nat Protoc 8:1743-58.
Metzker ML (2010) Sequencing technologies—the next generation. Nat Rev Genet 11:31-46.
Munsky B, et al. (2012) Using Gene Expression Noise to Understand Gene Regulation. Science 336:183-187.
Murgha YE, et al. (2014) Methods for the preparation of large quantities of complex single-stranded oligonucleotide libraries. PLoS One 9:1-10.
Raj A, et al. (2008) Imaging individual mRNA molecules using multiple singly labeled probes. Nat Methods 5:877-879.
Roberts, I., et al. "Novel method for the production of multiple colour chromosome paints for use in karyotyping by fluorescence in situ hybridisation." Genes, Chromosomes and Cancer 25.3 (1999): 241-250.
Sambrook et al., eds. Molecular Cloning: A Laboratory Manual, Chapter 10. 3rd ed., , Cold Spring Harbor Press, Cold Spring Harbor (2001).
Schröck, E., et al. "Multicolor spectral karyotyping of human chromosomes." Science 273.5274 (1996): 494-497.
Tijssen (1993) Laboratory Techniques in Biochemistry and Molecular Biology—Hybridization with Nucleic Acid Probes, part I chapter 2, "Overview of principles of hybridization and the strategy of nucleic acid probe assays" (Elsevier, N.Y.).
Uhlén M et al. (2015) Tissue-based map of the human proteome. Science 347:1260419.
Xiao L, GJ (2015) Multiplexed single-cell in situ RNA analysis by reiterative hybridization. Anal Methods 7:7290-7295.
Xu Q, et al (2009) Design of 240 , 000 orthogonal 25mer DNA barcode probes. 106:2289-2294.

```
                            SEQUENCE LISTING

<160> NUMBER OF SEQ ID NOS: 219

<210> SEQ ID NO 1
<211> LENGTH: 70
<212> TYPE: DNA
<213> ORGANISM: Artificial Sequence
<220> FEATURE:
<223> OTHER INFORMATION: synthetic

<400> SEQUENCE: 1
tcatccgata tggtgatcca ttttttcatc cgatatggtg atccattttt taacggctgc    60
ccattcattt                                                           70

<210> SEQ ID NO 2
<211> LENGTH: 70
<212> TYPE: DNA
<213> ORGANISM: Artificial Sequence
<220> FEATURE:
<223> OTHER INFORMATION: synthetic

<400> SEQUENCE: 2
tcatccgata tggtgatcca ttttttcatc cgatatggtg atccattttt ggagaaatcg    60
ggccagctag                                                           70

<210> SEQ ID NO 3
<211> LENGTH: 70
<212> TYPE: DNA
<213> ORGANISM: Artificial Sequence
<220> FEATURE:
<223> OTHER INFORMATION: synthetic

<400> SEQUENCE: 3
tcatccgata tggtgatcca ttttttcatc cgatatggtg atccattttt tctaggaaaa    60
gcatcacccg                                                           70

<210> SEQ ID NO 4
<211> LENGTH: 70
<212> TYPE: DNA
<213> ORGANISM: Artificial Sequence
<220> FEATURE:
<223> OTHER INFORMATION: synthetic

<400> SEQUENCE: 4
tcatccgata tggtgatcca ttttttcatc cgatatggtg atccattttt cccaatacga    60
ccaaatcaga                                                           70

<210> SEQ ID NO 5
<211> LENGTH: 70
<212> TYPE: DNA
<213> ORGANISM: Artificial Sequence
<220> FEATURE:
<223> OTHER INFORMATION: synthetic

<400> SEQUENCE: 5
tcatccgata tggtgatcca ttttttcatc cgatatggtg atccattttt cagagttaaa    60
agcagccctg                                                           70
```

```
<210> SEQ ID NO 6
<211> LENGTH: 70
<212> TYPE: DNA
<213> ORGANISM: Artificial Sequence
<220> FEATURE:
<223> OTHER INFORMATION: synthetic

<400> SEQUENCE: 6
tcatccgata tggtgatcca tttttcatc cgatatggtg atccattttt gggtcattga      60
tggcaacaat                                                            70

<210> SEQ ID NO 7
<211> LENGTH: 70
<212> TYPE: DNA
<213> ORGANISM: Artificial Sequence
<220> FEATURE:
<223> OTHER INFORMATION: synthetic

<400> SEQUENCE: 7
tcatccgata tggtgatcca tttttcatc cgatatggtg atccattttt accatgtagt      60
tgaggtcaat                                                            70

<210> SEQ ID NO 8
<211> LENGTH: 70
<212> TYPE: DNA
<213> ORGANISM: Artificial Sequence
<220> FEATURE:
<223> OTHER INFORMATION: synthetic

<400> SEQUENCE: 8
tcatccgata tggtgatcca tttttcatc cgatatggtg atccattttt catgggtgga      60
atcatattgg                                                            70

<210> SEQ ID NO 9
<211> LENGTH: 70
<212> TYPE: DNA
<213> ORGANISM: Artificial Sequence
<220> FEATURE:
<223> OTHER INFORMATION: synthetic

<400> SEQUENCE: 9
tcatccgata tggtgatcca tttttcatc cgatatggtg atccattttt ttgacggtgc      60
catggaattt                                                            70

<210> SEQ ID NO 10
<211> LENGTH: 70
<212> TYPE: DNA
<213> ORGANISM: Artificial Sequence
<220> FEATURE:
<223> OTHER INFORMATION: synthetic

<400> SEQUENCE: 10
tcatccgata tggtgatcca tttttcatc cgatatggtg atccattttt cattgatgac      60
aagcttcccg                                                            70

<210> SEQ ID NO 11
<211> LENGTH: 70
<212> TYPE: DNA
<213> ORGANISM: Artificial Sequence
<220> FEATURE:
<223> OTHER INFORMATION: synthetic
```

```
<400> SEQUENCE: 11
tcatccgata tggtgatcca ttttttcatc cgatatggtg atccattttt ctggaagatg    60
gtgatgggat                                                           70

<210> SEQ ID NO 12
<211> LENGTH: 70
<212> TYPE: DNA
<213> ORGANISM: Artificial Sequence
<220> FEATURE:
<223> OTHER INFORMATION: synthetic

<400> SEQUENCE: 12
tcatccgata tggtgatcca ttttttcatc cgatatggtg atccattttt cttgattttg    60
gagggatctc                                                           70

<210> SEQ ID NO 13
<211> LENGTH: 70
<212> TYPE: DNA
<213> ORGANISM: Artificial Sequence
<220> FEATURE:
<223> OTHER INFORMATION: synthetic

<400> SEQUENCE: 13
tcatccgata tggtgatcca ttttttcatc cgatatggtg atccattttt cagtggactc    60
cacgacgtac                                                           70

<210> SEQ ID NO 14
<211> LENGTH: 70
<212> TYPE: DNA
<213> ORGANISM: Artificial Sequence
<220> FEATURE:
<223> OTHER INFORMATION: synthetic

<400> SEQUENCE: 14
tcatccgata tggtgatcca ttttttcatc cgatatggtg atccattttt ttctccatgg    60
tggtgaagac                                                           70

<210> SEQ ID NO 15
<211> LENGTH: 70
<212> TYPE: DNA
<213> ORGANISM: Artificial Sequence
<220> FEATURE:
<223> OTHER INFORMATION: synthetic

<400> SEQUENCE: 15
tcatccgata tggtgatcca ttttttcatc cgatatggtg atccattttt agagatgatg    60
acccttttgg                                                           70

<210> SEQ ID NO 16
<211> LENGTH: 70
<212> TYPE: DNA
<213> ORGANISM: Artificial Sequence
<220> FEATURE:
<223> OTHER INFORMATION: synthetic

<400> SEQUENCE: 16
tcatccgata tggtgatcca ttttttcatc cgatatggtg atccattttt atgacgaaca    60
tgggggcatc                                                           70
```

```
<210> SEQ ID NO 17
<211> LENGTH: 70
<212> TYPE: DNA
<213> ORGANISM: Artificial Sequence
<220> FEATURE:
<223> OTHER INFORMATION: synthetic

<400> SEQUENCE: 17
tcatccgata tggtgatcca tttttcatc cgatatggtg atccattttt gtcatacttc      60
tcatggttca                                                            70

<210> SEQ ID NO 18
<211> LENGTH: 70
<212> TYPE: DNA
<213> ORGANISM: Artificial Sequence
<220> FEATURE:
<223> OTHER INFORMATION: synthetic

<400> SEQUENCE: 18
tcatccgata tggtgatcca tttttcatc cgatatggtg atccattttt attgctgatg      60
atcttgaggc                                                            70

<210> SEQ ID NO 19
<211> LENGTH: 70
<212> TYPE: DNA
<213> ORGANISM: Artificial Sequence
<220> FEATURE:
<223> OTHER INFORMATION: synthetic

<400> SEQUENCE: 19
tcatccgata tggtgatcca tttttcatc cgatatggtg atccattttt ctaagcagtt      60
ggtggtgcag                                                            70

<210> SEQ ID NO 20
<211> LENGTH: 70
<212> TYPE: DNA
<213> ORGANISM: Artificial Sequence
<220> FEATURE:
<223> OTHER INFORMATION: synthetic

<400> SEQUENCE: 20
tcatccgata tggtgatcca tttttcatc cgatatggtg atccattttt agttgtcatg      60
gatgaccttg                                                            70

<210> SEQ ID NO 21
<211> LENGTH: 70
<212> TYPE: DNA
<213> ORGANISM: Artificial Sequence
<220> FEATURE:
<223> OTHER INFORMATION: synthetic

<400> SEQUENCE: 21
tcatccgata tggtgatcca tttttcatc cgatatggtg atccattttt catgagtcct      60
tccacgatac                                                            70

<210> SEQ ID NO 22
<211> LENGTH: 70
<212> TYPE: DNA
<213> ORGANISM: Artificial Sequence
<220> FEATURE:
<223> OTHER INFORMATION: synthetic
```

```
<400> SEQUENCE: 22
tcatccgata tggtgatcca ttttttcatc cgatatggtg atccattttt cagtgatggc    60
atggactgtg                                                           70

<210> SEQ ID NO 23
<211> LENGTH: 70
<212> TYPE: DNA
<213> ORGANISM: Artificial Sequence
<220> FEATURE:
<223> OTHER INFORMATION: synthetic

<400> SEQUENCE: 23
tcatccgata tggtgatcca ttttttcatc cgatatggtg atccattttt tagaggcagg    60
gatgatgttc                                                           70

<210> SEQ ID NO 24
<211> LENGTH: 70
<212> TYPE: DNA
<213> ORGANISM: Artificial Sequence
<220> FEATURE:
<223> OTHER INFORMATION: synthetic

<400> SEQUENCE: 24
tcatccgata tggtgatcca ttttttcatc cgatatggtg atccattttt tcagctcagg    60
gatgaccttg                                                           70

<210> SEQ ID NO 25
<211> LENGTH: 70
<212> TYPE: DNA
<213> ORGANISM: Artificial Sequence
<220> FEATURE:
<223> OTHER INFORMATION: synthetic

<400> SEQUENCE: 25
tcatccgata tggtgatcca ttttttcatc cgatatggtg atccattttt cactgacacg    60
ttggcagtgg                                                           70

<210> SEQ ID NO 26
<211> LENGTH: 70
<212> TYPE: DNA
<213> ORGANISM: Artificial Sequence
<220> FEATURE:
<223> OTHER INFORMATION: synthetic

<400> SEQUENCE: 26
tcatccgata tggtgatcca ttttttcatc cgatatggtg atccattttt ttggcaggtt    60
tttctagacg                                                           70

<210> SEQ ID NO 27
<211> LENGTH: 70
<212> TYPE: DNA
<213> ORGANISM: Artificial Sequence
<220> FEATURE:
<223> OTHER INFORMATION: synthetic

<400> SEQUENCE: 27
tcatccgata tggtgatcca ttttttcatc cgatatggtg atccattttt caccttcttg    60
atgtcatcat                                                           70
```

```
<210> SEQ ID NO 28
<211> LENGTH: 70
<212> TYPE: DNA
<213> ORGANISM: Artificial Sequence
<220> FEATURE:
<223> OTHER INFORMATION: synthetic

<400> SEQUENCE: 28
tcatccgata tggtgatcca tttttcatc cgatatggtg atccattttt gctgttgaag        60
tcagaggaga                                                               70

<210> SEQ ID NO 29
<211> LENGTH: 70
<212> TYPE: DNA
<213> ORGANISM: Artificial Sequence
<220> FEATURE:
<223> OTHER INFORMATION: synthetic

<400> SEQUENCE: 29
tcatccgata tggtgatcca tttttcatc cgatatggtg atccattttt cgtcaaaggt        60
ggaggagtgg                                                               70

<210> SEQ ID NO 30
<211> LENGTH: 70
<212> TYPE: DNA
<213> ORGANISM: Artificial Sequence
<220> FEATURE:
<223> OTHER INFORMATION: synthetic

<400> SEQUENCE: 30
tcatccgata tggtgatcca tttttcatc cgatatggtg atccattttt aaagtggtcg        60
ttgagggcaa                                                               70

<210> SEQ ID NO 31
<211> LENGTH: 70
<212> TYPE: DNA
<213> ORGANISM: Artificial Sequence
<220> FEATURE:
<223> OTHER INFORMATION: synthetic

<400> SEQUENCE: 31
tcatccgata tggtgatcca tttttcatc cgatatggtg atccattttt gtcataccag        60
gaaatgagct                                                               70

<210> SEQ ID NO 32
<211> LENGTH: 70
<212> TYPE: DNA
<213> ORGANISM: Artificial Sequence
<220> FEATURE:
<223> OTHER INFORMATION: synthetic

<400> SEQUENCE: 32
tcatccgata tggtgatcca tttttcatc cgatatggtg atccattttt tgttgctgta        60
gccaaattcg                                                               70

<210> SEQ ID NO 33
<211> LENGTH: 70
<212> TYPE: DNA
<213> ORGANISM: Artificial Sequence
<220> FEATURE:
<223> OTHER INFORMATION: synthetic
```

<400> SEQUENCE: 33
tcatccgata tggtgatcca ttttttcatc cgatatggtg atccattttt cagtgagggt    60
ctctctcttc    70

<210> SEQ ID NO 34
<211> LENGTH: 70
<212> TYPE: DNA
<213> ORGANISM: Artificial Sequence
<220> FEATURE:
<223> OTHER INFORMATION: synthetic

<400> SEQUENCE: 34
tcatccgata tggtgatcca ttttttcatc cgatatggtg atccattttt aactgtgagg    60
aggggagatt    70

<210> SEQ ID NO 35
<211> LENGTH: 70
<212> TYPE: DNA
<213> ORGANISM: Artificial Sequence
<220> FEATURE:
<223> OTHER INFORMATION: synthetic

<400> SEQUENCE: 35
tcatccgata tggtgatcca ttttttcatc cgatatggtg atccattttt ctcttcaagg    60
ggtctacatg    70

<210> SEQ ID NO 36
<211> LENGTH: 70
<212> TYPE: DNA
<213> ORGANISM: Artificial Sequence
<220> FEATURE:
<223> OTHER INFORMATION: synthetic

<400> SEQUENCE: 36
tcatccgata tggtgatcca ttttttcatc cgatatggtg atccattttt atggtacatg    60
acaaggtgcg    70

<210> SEQ ID NO 37
<211> LENGTH: 70
<212> TYPE: DNA
<213> ORGANISM: Artificial Sequence
<220> FEATURE:
<223> OTHER INFORMATION: synthetic

<400> SEQUENCE: 37
tcatccgata tggtgatcca ttttttcatc cgatatggtg atccattttt ttaactggtt    60
gagcacaggg    70

<210> SEQ ID NO 38
<211> LENGTH: 70
<212> TYPE: DNA
<213> ORGANISM: Artificial Sequence
<220> FEATURE:
<223> OTHER INFORMATION: synthetic

<400> SEQUENCE: 38
gtctttacag atgtctgcgg ttttgtctt tacagatgtc tgcggttttt tgcattacca    60
gagactttct    70

<210> SEQ ID NO 39
<211> LENGTH: 70
<212> TYPE: DNA
<213> ORGANISM: Artificial Sequence
<220> FEATURE:
<223> OTHER INFORMATION: synthetic

<400> SEQUENCE: 39
gtctttacag atgtctgcgg tttttgtctt tacagatgtc tgcggttttt ggcttataac    60
caagctttgt                                                          70

<210> SEQ ID NO 40
<211> LENGTH: 70
<212> TYPE: DNA
<213> ORGANISM: Artificial Sequence
<220> FEATURE:
<223> OTHER INFORMATION: synthetic

<400> SEQUENCE: 40
gtctttacag atgtctgcgg tttttgtctt tacagatgtc tgcggttttt tggagttttc    60
ctaggactag                                                          70

<210> SEQ ID NO 41
<211> LENGTH: 70
<212> TYPE: DNA
<213> ORGANISM: Artificial Sequence
<220> FEATURE:
<223> OTHER INFORMATION: synthetic

<400> SEQUENCE: 41
gtctttacag atgtctgcgg tttttgtctt tacagatgtc tgcggttttt taggaacctc    60
tgtctgagat                                                          70

<210> SEQ ID NO 42
<211> LENGTH: 70
<212> TYPE: DNA
<213> ORGANISM: Artificial Sequence
<220> FEATURE:
<223> OTHER INFORMATION: synthetic

<400> SEQUENCE: 42
gtctttacag atgtctgcgg tttttgtctt tacagatgtc tgcggttttt agacactctc    60
tttgaaggca                                                          70

<210> SEQ ID NO 43
<211> LENGTH: 70
<212> TYPE: DNA
<213> ORGANISM: Artificial Sequence
<220> FEATURE:
<223> OTHER INFORMATION: synthetic

<400> SEQUENCE: 43
gtctttacag atgtctgcgg tttttgtctt tacagatgtc tgcggttttt gttcattgac    60
ctttgaggac                                                          70

<210> SEQ ID NO 44
<211> LENGTH: 70
<212> TYPE: DNA
<213> ORGANISM: Artificial Sequence
<220> FEATURE:
<223> OTHER INFORMATION: synthetic

```
<400> SEQUENCE: 44
gtctttacag atgtctgcgg ttttttgtctt tacagatgtc tgcggttttt cgtggcctgt    60
actaaattga                                                           70

<210> SEQ ID NO 45
<211> LENGTH: 70
<212> TYPE: DNA
<213> ORGANISM: Artificial Sequence
<220> FEATURE:
<223> OTHER INFORMATION: synthetic

<400> SEQUENCE: 45
gtctttacag atgtctgcgg ttttttgtctt tacagatgtc tgcggttttt agttgttgag    60
cactctgtag                                                           70

<210> SEQ ID NO 46
<211> LENGTH: 70
<212> TYPE: DNA
<213> ORGANISM: Artificial Sequence
<220> FEATURE:
<223> OTHER INFORMATION: synthetic

<400> SEQUENCE: 46
gtctttacag atgtctgcgg ttttttgtctt tacagatgtc tgcggttttt tctaatacac    60
tgccgtctta                                                           70

<210> SEQ ID NO 47
<211> LENGTH: 70
<212> TYPE: DNA
<213> ORGANISM: Artificial Sequence
<220> FEATURE:
<223> OTHER INFORMATION: synthetic

<400> SEQUENCE: 47
gtctttacag atgtctgcgg ttttttgtctt tacagatgtc tgcggttttt tgtttgcagt    60
ggatactgtt                                                           70

<210> SEQ ID NO 48
<211> LENGTH: 70
<212> TYPE: DNA
<213> ORGANISM: Artificial Sequence
<220> FEATURE:
<223> OTHER INFORMATION: synthetic

<400> SEQUENCE: 48
gtctttacag atgtctgcgg ttttttgtctt tacagatgtc tgcggttttt gtagcttctg    60
tatattcctg                                                           70

<210> SEQ ID NO 49
<211> LENGTH: 70
<212> TYPE: DNA
<213> ORGANISM: Artificial Sequence
<220> FEATURE:
<223> OTHER INFORMATION: synthetic

<400> SEQUENCE: 49
gtctttacag atgtctgcgg ttttttgtctt tacagatgtc tgcggttttt cgtgtctttc    60
atgagttctg                                                           70
```

<210> SEQ ID NO 50
<211> LENGTH: 70
<212> TYPE: DNA
<213> ORGANISM: Artificial Sequence
<220> FEATURE:
<223> OTHER INFORMATION: synthetic

<400> SEQUENCE: 50
gtctttacag atgtctgcgg tttttgtctt tacagatgtc tgcggttttt ctggttgtaa    60
tgactggcag                                                          70

<210> SEQ ID NO 51
<211> LENGTH: 70
<212> TYPE: DNA
<213> ORGANISM: Artificial Sequence
<220> FEATURE:
<223> OTHER INFORMATION: synthetic

<400> SEQUENCE: 51
gtctttacag atgtctgcgg tttttgtctt tacagatgtc tgcggttttt tcatcagtca    60
ttgattcctc                                                          70

<210> SEQ ID NO 52
<211> LENGTH: 70
<212> TYPE: DNA
<213> ORGANISM: Artificial Sequence
<220> FEATURE:
<223> OTHER INFORMATION: synthetic

<400> SEQUENCE: 52
gtctttacag atgtctgcgg tttttgtctt tacagatgtc tgcggttttt tttcctgata    60
cttctcttgg                                                          70

<210> SEQ ID NO 53
<211> LENGTH: 70
<212> TYPE: DNA
<213> ORGANISM: Artificial Sequence
<220> FEATURE:
<223> OTHER INFORMATION: synthetic

<400> SEQUENCE: 53
gtctttacag atgtctgcgg tttttgtctt tacagatgtc tgcggttttt ctgatggcat    60
tagattcctg                                                          70

<210> SEQ ID NO 54
<211> LENGTH: 70
<212> TYPE: DNA
<213> ORGANISM: Artificial Sequence
<220> FEATURE:
<223> OTHER INFORMATION: synthetic

<400> SEQUENCE: 54
gtctttacag atgtctgcgg tttttgtctt tacagatgtc tgcggttttt cttcacctac    60
tgatggttta                                                          70

<210> SEQ ID NO 55
<211> LENGTH: 70
<212> TYPE: DNA
<213> ORGANISM: Artificial Sequence
<220> FEATURE:
<223> OTHER INFORMATION: synthetic

<400> SEQUENCE: 55
gtctttacag atgtctgcgg tttttgtctt tacagatgtc tgcggttttt ctgagacttc    60
tcttggactg                                                          70

<210> SEQ ID NO 56
<211> LENGTH: 70
<212> TYPE: DNA
<213> ORGANISM: Artificial Sequence
<220> FEATURE:
<223> OTHER INFORMATION: synthetic

<400> SEQUENCE: 56
gtctttacag atgtctgcgg tttttgtctt tacagatgtc tgcggttttt tcctgagtgc    60
gaagaattct                                                          70

<210> SEQ ID NO 57
<211> LENGTH: 70
<212> TYPE: DNA
<213> ORGANISM: Artificial Sequence
<220> FEATURE:
<223> OTHER INFORMATION: synthetic

<400> SEQUENCE: 57
gtctttacag atgtctgcgg tttttgtctt tacagatgtc tgcggttttt tcgttagtca    60
ttgattcctc                                                          70

<210> SEQ ID NO 58
<211> LENGTH: 70
<212> TYPE: DNA
<213> ORGANISM: Artificial Sequence
<220> FEATURE:
<223> OTHER INFORMATION: synthetic

<400> SEQUENCE: 58
gtctttacag atgtctgcgg tttttgtctt tacagatgtc tgcggttttt tgtgacttgg    60
tgtctggaag                                                          70

<210> SEQ ID NO 59
<211> LENGTH: 70
<212> TYPE: DNA
<213> ORGANISM: Artificial Sequence
<220> FEATURE:
<223> OTHER INFORMATION: synthetic

<400> SEQUENCE: 59
gtctttacag atgtctgcgg tttttgtctt tacagatgtc tgcggttttt agctctgtag    60
gatactttgg                                                          70

<210> SEQ ID NO 60
<211> LENGTH: 70
<212> TYPE: DNA
<213> ORGANISM: Artificial Sequence
<220> FEATURE:
<223> OTHER INFORMATION: synthetic

<400> SEQUENCE: 60
gtctttacag atgtctgcgg tttttgtctt tacagatgtc tgcggttttt gtgttgatgt    60 cttttctcttc                                                         70

<210> SEQ ID NO 61
<211> LENGTH: 70
<212> TYPE: DNA
<213> ORGANISM: Artificial Sequence
<220> FEATURE:
<223> OTHER INFORMATION: synthetic

<400> SEQUENCE: 61
gtctttacag atgtctgcgg tttttgtctt tacagatgtc tgcggttttt tctattgctg    60
ccaggtaaat                                                           70

<210> SEQ ID NO 62
<211> LENGTH: 70
<212> TYPE: DNA
<213> ORGANISM: Artificial Sequence
<220> FEATURE:
<223> OTHER INFORMATION: synthetic

<400> SEQUENCE: 62
gtctttacag atgtctgcgg tttttgtctt tacagatgtc tgcggttttt tttccttacg    60
agtttgtagc                                                           70

<210> SEQ ID NO 63
<211> LENGTH: 70
<212> TYPE: DNA
<213> ORGANISM: Artificial Sequence
<220> FEATURE:
<223> OTHER INFORMATION: synthetic

<400> SEQUENCE: 63
gtctttacag atgtctgcgg tttttgtctt tacagatgtc tgcggttttt tggtgtctgg    60
aaaagctctc                                                           70

<210> SEQ ID NO 64
<211> LENGTH: 70
<212> TYPE: DNA
<213> ORGANISM: Artificial Sequence
<220> FEATURE:
<223> OTHER INFORMATION: synthetic

<400> SEQUENCE: 64
gtctttacag atgtctgcgg tttttgtctt tacagatgtc tgcggttttt tgattgcgga    60
gatttgcaga                                                           70

<210> SEQ ID NO 65
<211> LENGTH: 70
<212> TYPE: DNA
<213> ORGANISM: Artificial Sequence
<220> FEATURE:
<223> OTHER INFORMATION: synthetic

<400> SEQUENCE: 65
gtctttacag atgtctgcgg tttttgtctt tacagatgtc tgcggtttt gtgttgatgt     60 ctttctcttc                                                           70

<210> SEQ ID NO 66
<211> LENGTH: 70
<212> TYPE: DNA
<213> ORGANISM: Artificial Sequence
<220> FEATURE:
<223> OTHER INFORMATION: synthetic

<400> SEQUENCE: 66
gtctttacag atgtctgcgg tttttgtctt tacagatgtc tgcggttttt gtgattttgt    60
catcggtcat                                                             70

<210> SEQ ID NO 67
<211> LENGTH: 70
<212> TYPE: DNA
<213> ORGANISM: Artificial Sequence
<220> FEATURE:
<223> OTHER INFORMATION: synthetic

<400> SEQUENCE: 67
gtctttacag atgtctgcgg tttttgtctt tacagatgtc tgcggttttt aggatatctt    60
gagtcgttgc                                                             70

<210> SEQ ID NO 68
<211> LENGTH: 70
<212> TYPE: DNA
<213> ORGANISM: Artificial Sequence
<220> FEATURE:
<223> OTHER INFORMATION: synthetic

<400> SEQUENCE: 68
gtctttacag atgtctgcgg tttttgtctt tacagatgtc tgcggttttt ctggaagagc    60
tctttcaagc                                                             70

<210> SEQ ID NO 69
<211> LENGTH: 70
<212> TYPE: DNA
<213> ORGANISM: Artificial Sequence
<220> FEATURE:
<223> OTHER INFORMATION: synthetic

<400> SEQUENCE: 69
gtctttacag atgtctgcgg tttttgtctt tacagatgtc tgcggttttt ctgagacttc    60
tcttggactg                                                             70

<210> SEQ ID NO 70
<211> LENGTH: 70
<212> TYPE: DNA
<213> ORGANISM: Artificial Sequence
<220> FEATURE:
<223> OTHER INFORMATION: synthetic

<400> SEQUENCE: 70
gtctttacag atgtctgcgg tttttgtctt tacagatgtc tgcggttttt ctactgatgg    60
tgttcgtttc                                                             70

<210> SEQ ID NO 71
<211> LENGTH: 70
<212> TYPE: DNA
<213> ORGANISM: Artificial Sequence
<220> FEATURE:
<223> OTHER INFORMATION: synthetic

<400> SEQUENCE: 71
gtctttacag atgtctgcgg tttttgtctt tacagatgtc tgcggttttt tcatcagtca    60
ttgattcctc                                                             70

<210> SEQ ID NO 72
<211> LENGTH: 70
<212> TYPE: DNA
<213> ORGANISM: Artificial Sequence
<220> FEATURE:
<223> OTHER INFORMATION: synthetic

<400> SEQUENCE: 72
gtctttacag atgtctgcgg ttttgtctt tacagatgtc tgcggttttt ccttaaacgc    60
tttgatgctc                                                          70

<210> SEQ ID NO 73
<211> LENGTH: 70
<212> TYPE: DNA
<213> ORGANISM: Artificial Sequence
<220> FEATURE:
<223> OTHER INFORMATION: synthetic

<400> SEQUENCE: 73
gtctttacag atgtctgcgg ttttgtctt tacagatgtc tgcggttttt gcacgttgct    60
tcaatacttt                                                          70

<210> SEQ ID NO 74
<211> LENGTH: 70
<212> TYPE: DNA
<213> ORGANISM: Artificial Sequence
<220> FEATURE:
<223> OTHER INFORMATION: synthetic

<400> SEQUENCE: 74
gtctttacag atgtctgcgg ttttgtctt tacagatgtc tgcggttttt tttgcagatt    60
ccttcaatgc                                                          70

<210> SEQ ID NO 75
<211> LENGTH: 57
<212> TYPE: DNA
<213> ORGANISM: Artificial Sequence
<220> FEATURE:
<223> OTHER INFORMATION: synthetic

<400> SEQUENCE: 75
tcatccgata tggtgatcca ttttttctgt tccttgctcc ttgctttctc catactc      57

<210> SEQ ID NO 76
<211> LENGTH: 57
<212> TYPE: DNA
<213> ORGANISM: Artificial Sequence
<220> FEATURE:
<223> OTHER INFORMATION: synthetic

<400> SEQUENCE: 76
tcatccgata tggtgatcca tttttcttga acaccttttc caactcaccg tgctggt      57

<210> SEQ ID NO 77
<211> LENGTH: 57
<212> TYPE: DNA
<213> ORGANISM: Artificial Sequence
<220> FEATURE:
<223> OTHER INFORMATION: synthetic

<400> SEQUENCE: 77
tcatccgata tggtgatcca tttttggcat tctcttcaaa cctccaggta ttgtgta      57

```
<210> SEQ ID NO 78
<211> LENGTH: 57
<212> TYPE: DNA
<213> ORGANISM: Artificial Sequence
<220> FEATURE:
<223> OTHER INFORMATION: synthetic

<400> SEQUENCE: 78
tcatccgata tggtgatcca tttttgttac agcataagat agaccgtaaa agccaac      57

<210> SEQ ID NO 79
<211> LENGTH: 57
<212> TYPE: DNA
<213> ORGANISM: Artificial Sequence
<220> FEATURE:
<223> OTHER INFORMATION: synthetic

<400> SEQUENCE: 79
tcatccgata tggtgatcca tttttcccag aagtcattgc taaagcagga aggccca      57

<210> SEQ ID NO 80
<211> LENGTH: 57
<212> TYPE: DNA
<213> ORGANISM: Artificial Sequence
<220> FEATURE:
<223> OTHER INFORMATION: synthetic

<400> SEQUENCE: 80
tcatccgata tggtgatcca tttttatgat ggcaatcctg gatgagtgtt ttagtct      57

<210> SEQ ID NO 81
<211> LENGTH: 57
<212> TYPE: DNA
<213> ORGANISM: Artificial Sequence
<220> FEATURE:
<223> OTHER INFORMATION: synthetic

<400> SEQUENCE: 81
tcatccgata tggtgatcca ttttttctgc cattagctgt gggtcgatcg tgtccta      57

<210> SEQ ID NO 82
<211> LENGTH: 57
<212> TYPE: DNA
<213> ORGANISM: Artificial Sequence
<220> FEATURE:
<223> OTHER INFORMATION: synthetic

<400> SEQUENCE: 82
tcatccgata tggtgatcca tttttagtg tcccagatag cagagaggct agtgtga       57

<210> SEQ ID NO 83
<211> LENGTH: 57
<212> TYPE: DNA
<213> ORGANISM: Artificial Sequence
<220> FEATURE:
<223> OTHER INFORMATION: synthetic

<400> SEQUENCE: 83
tcatccgata tggtgatcca tttttactga gtgtgagttt ccagcccagg gtgctgg      57

<210> SEQ ID NO 84
<211> LENGTH: 57
<212> TYPE: DNA
<213> ORGANISM: Artificial Sequence
<220> FEATURE:
<223> OTHER INFORMATION: synthetic
```

<400> SEQUENCE: 84
tcatccgata tggtgatcca tttttctcaa gagccctatt catgggagtg gactctt    57

<210> SEQ ID NO 85
<211> LENGTH: 57
<212> TYPE: DNA
<213> ORGANISM: Artificial Sequence
<220> FEATURE:
<223> OTHER INFORMATION: synthetic

<400> SEQUENCE: 85
tcatccgata tggtgatcca tttttctgca gagcccaaga taagagatgg ccctgag    57

<210> SEQ ID NO 86
<211> LENGTH: 57
<212> TYPE: DNA
<213> ORGANISM: Artificial Sequence
<220> FEATURE:
<223> OTHER INFORMATION: synthetic

<400> SEQUENCE: 86
tcatccgata tggtgatcca tttttgtcat actgtgccta atgaatcact ggatata    57

<210> SEQ ID NO 87
<211> LENGTH: 57
<212> TYPE: DNA
<213> ORGANISM: Artificial Sequence
<220> FEATURE:
<223> OTHER INFORMATION: synthetic

<400> SEQUENCE: 87
tcatccgata tggtgatcca tttttagctc aacccaggag aaggatttgt tcttgga    57

<210> SEQ ID NO 88
<211> LENGTH: 57
<212> TYPE: DNA
<213> ORGANISM: Artificial Sequence
<220> FEATURE:
<223> OTHER INFORMATION: synthetic

<400> SEQUENCE: 88
tcatccgata tggtgatcca tttttttat agggagtcct gactattctt gttctgt    57

<210> SEQ ID NO 89
<211> LENGTH: 57
<212> TYPE: DNA
<213> ORGANISM: Artificial Sequence
<220> FEATURE:
<223> OTHER INFORMATION: synthetic

<400> SEQUENCE: 89
tcatccgata tggtgatcca tttttccttc agtcttcaac tcttgatacc tgttaat    57

<210> SEQ ID NO 90
<211> LENGTH: 57
<212> TYPE: DNA
<213> ORGANISM: Artificial Sequence
<220> FEATURE:
<223> OTHER INFORMATION: synthetic

<400> SEQUENCE: 90
tcatccgata tggtgatcca tttttttataa acataggcat gctcaagtta agtgcct    57

<210> SEQ ID NO 91
<211> LENGTH: 57
<212> TYPE: DNA
<213> ORGANISM: Artificial Sequence
<220> FEATURE:
<223> OTHER INFORMATION: synthetic

<400> SEQUENCE: 91
tcatccgata tggtgatcca tttttagggt tcaaacttgg tggtgtccag gtagcta        57

<210> SEQ ID NO 92
<211> LENGTH: 57
<212> TYPE: DNA
<213> ORGANISM: Artificial Sequence
<220> FEATURE:
<223> OTHER INFORMATION: synthetic

<400> SEQUENCE: 92
tcatccgata tggtgatcca tttttacaaa gcacctaatt gggaaacaca tggctct        57

<210> SEQ ID NO 93
<211> LENGTH: 57
<212> TYPE: DNA
<213> ORGANISM: Artificial Sequence
<220> FEATURE:
<223> OTHER INFORMATION: synthetic

<400> SEQUENCE: 93
tcatccgata tggtgatcca tttttaatag cttcagaaga cagtaatgca gcatgag        57

<210> SEQ ID NO 94
<211> LENGTH: 57
<212> TYPE: DNA
<213> ORGANISM: Artificial Sequence
<220> FEATURE:
<223> OTHER INFORMATION: synthetic

<400> SEQUENCE: 94
tcatccgata tggtgatcca ttttctag cacattggtt actgaggacc agaaggt        57

<210> SEQ ID NO 95
<211> LENGTH: 57
<212> TYPE: DNA
<213> ORGANISM: Artificial Sequence
<220> FEATURE:
<223> OTHER INFORMATION: synthetic

<400> SEQUENCE: 95
tcatccgata tggtgatcca tttttgcagg gaactaatac agtattacct gctttga        57

<210> SEQ ID NO 96
<211> LENGTH: 57
<212> TYPE: DNA
<213> ORGANISM: Artificial Sequence
<220> FEATURE:
<223> OTHER INFORMATION: synthetic

<400> SEQUENCE: 96
tcatccgata tggtgatcca tttttttctta atgcaggaag ttgtacaaat gcctcca        57

<210> SEQ ID NO 97
<211> LENGTH: 57
<212> TYPE: DNA
<213> ORGANISM: Artificial Sequence
<220> FEATURE:
<223> OTHER INFORMATION: synthetic

<400> SEQUENCE: 97
tcatccgata tggtgatcca tttttgtgct gtaacctctc accatgttta aggttgc    57

<210> SEQ ID NO 98
<211> LENGTH: 57
<212> TYPE: DNA
<213> ORGANISM: Artificial Sequence
<220> FEATURE:
<223> OTHER INFORMATION: synthetic

<400> SEQUENCE: 98
tcatccgata tggtgatcca tttttcata tttgacctga atcttagaac ctagcca    57

<210> SEQ ID NO 99
<211> LENGTH: 57
<212> TYPE: DNA
<213> ORGANISM: Artificial Sequence
<220> FEATURE:
<223> OTHER INFORMATION: synthetic

<400> SEQUENCE: 99
tcatccgata tggtgatcca tttttcaaa ccaatcatag gaaagcagca gtgcagt    57

<210> SEQ ID NO 100
<211> LENGTH: 57
<212> TYPE: DNA
<213> ORGANISM: Artificial Sequence
<220> FEATURE:
<223> OTHER INFORMATION: synthetic

<400> SEQUENCE: 100
tcatccgata tggtgatcca tttttcatta ggtggctgag tccaaaatgt cctcatc    57

<210> SEQ ID NO 101
<211> LENGTH: 57
<212> TYPE: DNA
<213> ORGANISM: Artificial Sequence
<220> FEATURE:
<223> OTHER INFORMATION: synthetic

<400> SEQUENCE: 101
tcatccgata tggtgatcca tttttaggaa gtatgtatgt tgggagcttc tgggctc    57

<210> SEQ ID NO 102
<211> LENGTH: 57
<212> TYPE: DNA
<213> ORGANISM: Artificial Sequence
<220> FEATURE:
<223> OTHER INFORMATION: synthetic

<400> SEQUENCE: 102
tcatccgata tggtgatcca tttttccagg acagctgtgc cagaactgcc ctgtgtg    57

<210> SEQ ID NO 103
<211> LENGTH: 57
<212> TYPE: DNA
<213> ORGANISM: Artificial Sequence
<220> FEATURE:
<223> OTHER INFORMATION: synthetic

<400> SEQUENCE: 103
tcatccgata tggtgatcca tttttggtgt cattatgtgt cggttttctc aactata    57

```
<210> SEQ ID NO 104
<211> LENGTH: 57
<212> TYPE: DNA
<213> ORGANISM: Artificial Sequence
<220> FEATURE:
<223> OTHER INFORMATION: synthetic

<400> SEQUENCE: 104
tcatccgata tggtgatcca tttttggatt gtccatatta tcatccatct gttaggt      57

<210> SEQ ID NO 105
<211> LENGTH: 57
<212> TYPE: DNA
<213> ORGANISM: Artificial Sequence
<220> FEATURE:
<223> OTHER INFORMATION: synthetic

<400> SEQUENCE: 105
tcatccgata tggtgatcca tttttgggtt tcaaatgatt cacaagtttt ccagtca      57

<210> SEQ ID NO 106
<211> LENGTH: 57
<212> TYPE: DNA
<213> ORGANISM: Artificial Sequence
<220> FEATURE:
<223> OTHER INFORMATION: synthetic

<400> SEQUENCE: 106
tcatccgata tggtgatcca tttttttgtta gcatgaggaa tcagatacaa ggtttga     57

<210> SEQ ID NO 107
<211> LENGTH: 57
<212> TYPE: DNA
<213> ORGANISM: Artificial Sequence
<220> FEATURE:
<223> OTHER INFORMATION: synthetic

<400> SEQUENCE: 107
tcatccgata tggtgatcca ttttttactgt gtgtaaatta caggagggac cttaaat     57

<210> SEQ ID NO 108
<211> LENGTH: 57
<212> TYPE: DNA
<213> ORGANISM: Artificial Sequence
<220> FEATURE:
<223> OTHER INFORMATION: synthetic

<400> SEQUENCE: 108
tcatccgata tggtgatcca tttttgagag ctggtaatac aaggtagcca gaggtct      57

<210> SEQ ID NO 109
<211> LENGTH: 57
<212> TYPE: DNA
<213> ORGANISM: Artificial Sequence
<220> FEATURE:
<223> OTHER INFORMATION: synthetic

<400> SEQUENCE: 109
tcatccgata tggtgatcca tttttcgact agattcaaac atgtttcctt tccttgg      57

<210> SEQ ID NO 110
<211> LENGTH: 57
<212> TYPE: DNA
<213> ORGANISM: Artificial Sequence
<220> FEATURE:
<223> OTHER INFORMATION: synthetic
```

<400> SEQUENCE: 110
tcatccgata tggtgatcca tttttagtca catgtgatac tgtgtattag tgatggg    57

<210> SEQ ID NO 111
<211> LENGTH: 57
<212> TYPE: DNA
<213> ORGANISM: Artificial Sequence
<220> FEATURE:
<223> OTHER INFORMATION: synthetic

<400> SEQUENCE: 111
tcatccgata tggtgatcca tttttttgact gccctggtga atgtgagatg tctggac    57

<210> SEQ ID NO 112
<211> LENGTH: 57
<212> TYPE: DNA
<213> ORGANISM: Artificial Sequence
<220> FEATURE:
<223> OTHER INFORMATION: synthetic

<400> SEQUENCE: 112
tcatccgata tggtgatcca tttttgcagc tcagagtggc ctttgacagc ataaagc    57

<210> SEQ ID NO 113
<211> LENGTH: 57
<212> TYPE: DNA
<213> ORGANISM: Artificial Sequence
<220> FEATURE:
<223> OTHER INFORMATION: synthetic

<400> SEQUENCE: 113
tcatccgata tggtgatcca tttttgcgta tgactgacat cacttccatc attttgg    57

<210> SEQ ID NO 114
<211> LENGTH: 57
<212> TYPE: DNA
<213> ORGANISM: Artificial Sequence
<220> FEATURE:
<223> OTHER INFORMATION: synthetic

<400> SEQUENCE: 114
tcatccgata tggtgatcca tttttgtggt gtcagtactt ctggcagtgg ctatgtg    57

<210> SEQ ID NO 115
<211> LENGTH: 57
<212> TYPE: DNA
<213> ORGANISM: Artificial Sequence
<220> FEATURE:
<223> OTHER INFORMATION: synthetic

<400> SEQUENCE: 115
tcatccgata tggtgatcca tttttgcttg tgtgcaggga tgacttaaag gaagtct    57

<210> SEQ ID NO 116
<211> LENGTH: 57
<212> TYPE: DNA
<213> ORGANISM: Artificial Sequence
<220> FEATURE:
<223> OTHER INFORMATION: synthetic

<400> SEQUENCE: 116
tcatccgata tggtgatcca tttttgcctg tgactaagat gaaggtacct tcttagc    57

<210> SEQ ID NO 117
<211> LENGTH: 57
<212> TYPE: DNA
<213> ORGANISM: Artificial Sequence
<220> FEATURE:
<223> OTHER INFORMATION: synthetic

<400> SEQUENCE: 117
tcatccgata tggtgatcca tttttgtgg gaaacattcc tcacctggat catcctt            57

<210> SEQ ID NO 118
<211> LENGTH: 57
<212> TYPE: DNA
<213> ORGANISM: Artificial Sequence
<220> FEATURE:
<223> OTHER INFORMATION: synthetic

<400> SEQUENCE: 118
tcatccgata tggtgatcca tttttcttga gtccaatgcc caacacatca gatctgg            57

<210> SEQ ID NO 119
<211> LENGTH: 57
<212> TYPE: DNA
<213> ORGANISM: Artificial Sequence
<220> FEATURE:
<223> OTHER INFORMATION: synthetic

<400> SEQUENCE: 119
tcatccgata tggtgatcca tttttggctc tctccaaatg atagtttgta agatgtc            57

<210> SEQ ID NO 120
<211> LENGTH: 57
<212> TYPE: DNA
<213> ORGANISM: Artificial Sequence
<220> FEATURE:
<223> OTHER INFORMATION: synthetic

<400> SEQUENCE: 120
tcatccgata tggtgatcca tttttgctg ttagtgtctg cagtgggaaa tggtgac            57

<210> SEQ ID NO 121
<211> LENGTH: 57
<212> TYPE: DNA
<213> ORGANISM: Artificial Sequence
<220> FEATURE:
<223> OTHER INFORMATION: synthetic

<400> SEQUENCE: 121
tcatccgata tggtgatcca tttttcaatg ttgccctagt gtctatatag accttgc            57

<210> SEQ ID NO 122
<211> LENGTH: 57
<212> TYPE: DNA
<213> ORGANISM: Artificial Sequence
<220> FEATURE:
<223> OTHER INFORMATION: synthetic

<400> SEQUENCE: 122
tcatccgata tggtgatcca tttttgtgtg gtaaagggcc gggtattggg aagctga            57

<210> SEQ ID NO 123
<211> LENGTH: 57
<212> TYPE: DNA
<213> ORGANISM: Artificial Sequence
<220> FEATURE:
<223> OTHER INFORMATION: synthetic

<400> SEQUENCE: 123
tcatccgata tggtgatcca tttttctgac ttctcagctc tgagcaaggc atttcag    57

<210> SEQ ID NO 124
<211> LENGTH: 57
<212> TYPE: DNA
<213> ORGANISM: Artificial Sequence
<220> FEATURE:
<223> OTHER INFORMATION: synthetic

<400> SEQUENCE: 124
tcatccgata tggtgatcca tttttcctgc agaatctgaa acttgagcat ttacctg    57

<210> SEQ ID NO 125
<211> LENGTH: 57
<212> TYPE: DNA
<213> ORGANISM: Artificial Sequence
<220> FEATURE:
<223> OTHER INFORMATION: synthetic

<400> SEQUENCE: 125
tcatccgata tggtgatcca tttttatcct caggtttcaa atgacataca tgatgga    57

<210> SEQ ID NO 126
<211> LENGTH: 57
<212> TYPE: DNA
<213> ORGANISM: Artificial Sequence
<220> FEATURE:
<223> OTHER INFORMATION: synthetic

<400> SEQUENCE: 126
tcatccgata tggtgatcca tttttgccag cttggtcaga aagtttcagc ttcatat    57

<210> SEQ ID NO 127
<211> LENGTH: 57
<212> TYPE: DNA
<213> ORGANISM: Artificial Sequence
<220> FEATURE:
<223> OTHER INFORMATION: synthetic

<400> SEQUENCE: 127
tcatccgata tggtgatcca tttttttggat gcttcattgt aagaggcctg tcctgtg    57

<210> SEQ ID NO 128
<211> LENGTH: 57
<212> TYPE: DNA
<213> ORGANISM: Artificial Sequence
<220> FEATURE:
<223> OTHER INFORMATION: synthetic

<400> SEQUENCE: 128
tcatccgata tggtgatcca tttttttgttc ttctagatgt ctgtggcact ccctgag    57

<210> SEQ ID NO 129
<211> LENGTH: 57
<212> TYPE: DNA
<213> ORGANISM: Artificial Sequence
<220> FEATURE:
<223> OTHER INFORMATION: synthetic

<400> SEQUENCE: 129
tcatccgata tggtgatcca tttttaaatg tctacacatc ctgtcttccc tgaggag    57

<210> SEQ ID NO 130
<211> LENGTH: 57
<212> TYPE: DNA
<213> ORGANISM: Artificial Sequence
<220> FEATURE:
<223> OTHER INFORMATION: synthetic

<400> SEQUENCE: 130
tcatccgata tggtgatcca tttttaggta tgtcttgggt cactttacag actggat            57

<210> SEQ ID NO 131
<211> LENGTH: 57
<212> TYPE: DNA
<213> ORGANISM: Artificial Sequence
<220> FEATURE:
<223> OTHER INFORMATION: synthetic

<400> SEQUENCE: 131
tcatccgata tggtgatcca tttttcttct ccatgatgtt caaatgggag aataaac            57

<210> SEQ ID NO 132
<211> LENGTH: 57
<212> TYPE: DNA
<213> ORGANISM: Artificial Sequence
<220> FEATURE:
<223> OTHER INFORMATION: synthetic

<400> SEQUENCE: 132
tcatccgata tggtgatcca tttttgaaat ctaatttcct caaggtagct cctaggg            57

<210> SEQ ID NO 133
<211> LENGTH: 57
<212> TYPE: DNA
<213> ORGANISM: Artificial Sequence
<220> FEATURE:
<223> OTHER INFORMATION: synthetic

<400> SEQUENCE: 133
tcatccgata tggtgatcca tttttttgctg tcttcacttt gaagaattct tgaccac            57

<210> SEQ ID NO 134
<211> LENGTH: 57
<212> TYPE: DNA
<213> ORGANISM: Artificial Sequence
<220> FEATURE:
<223> OTHER INFORMATION: synthetic

<400> SEQUENCE: 134
tcatccgata tggtgatcca ttttttttgtg atacagcttg caactccaca ccctggt            57

<210> SEQ ID NO 135
<211> LENGTH: 57
<212> TYPE: DNA
<213> ORGANISM: Artificial Sequence
<220> FEATURE:
<223> OTHER INFORMATION: synthetic

<400> SEQUENCE: 135
tcatccgata tggtgatcca tttttcagga cattgtactg caggaattgg aatctga            57

<210> SEQ ID NO 136
<211> LENGTH: 57
<212> TYPE: DNA
<213> ORGANISM: Artificial Sequence
<220> FEATURE:
<223> OTHER INFORMATION: synthetic

<400> SEQUENCE: 136
tcatccgata tggtgatcca ttttttttgta ggttcctcta tgtgctgctt ttccaga        57

<210> SEQ ID NO 137
<211> LENGTH: 57
<212> TYPE: DNA
<213> ORGANISM: Artificial Sequence
<220> FEATURE:
<223> OTHER INFORMATION: synthetic

<400> SEQUENCE: 137
tcatccgata tggtgatcca tttttgatct tctaatcacc tcccagggtc tggctgg        57

<210> SEQ ID NO 138
<211> LENGTH: 57
<212> TYPE: DNA
<213> ORGANISM: Artificial Sequence
<220> FEATURE:
<223> OTHER INFORMATION: synthetic

<400> SEQUENCE: 138
tcatccgata tggtgatcca tttttctaat gcacgtgact aatccttaga ctgctta        57

<210> SEQ ID NO 139
<211> LENGTH: 57
<212> TYPE: DNA
<213> ORGANISM: Artificial Sequence
<220> FEATURE:
<223> OTHER INFORMATION: synthetic

<400> SEQUENCE: 139
tcatccgata tggtgatcca tttttgatga ccaagtggga ttgaacttct gtccggt        57

<210> SEQ ID NO 140
<211> LENGTH: 57
<212> TYPE: DNA
<213> ORGANISM: Artificial Sequence
<220> FEATURE:
<223> OTHER INFORMATION: synthetic

<400> SEQUENCE: 140
tcatccgata tggtgatcca tttttttcaat gacttcttag ggtacccttg aaggagc       57

<210> SEQ ID NO 141
<211> LENGTH: 57
<212> TYPE: DNA
<213> ORGANISM: Artificial Sequence
<220> FEATURE:
<223> OTHER INFORMATION: synthetic

<400> SEQUENCE: 141
tcatccgata tggtgatcca tttttcacag cagtccatat tcagttagct ctcatat        57

<210> SEQ ID NO 142
<211> LENGTH: 57
<212> TYPE: DNA
<213> ORGANISM: Artificial Sequence
<220> FEATURE:
<223> OTHER INFORMATION: synthetic

<400> SEQUENCE: 142
tcatccgata tggtgatcca tttttttccat ctgtaaacta ggatgagtag ttttccc       57

<210> SEQ ID NO 143
<211> LENGTH: 57
<212> TYPE: DNA
<213> ORGANISM: Artificial Sequence
<220> FEATURE:
<223> OTHER INFORMATION: synthetic

<400> SEQUENCE: 143
tcatccgata tggtgatcca tttttggttt gagctgataa gacatagaag tactaca      57

<210> SEQ ID NO 144
<211> LENGTH: 57
<212> TYPE: DNA
<213> ORGANISM: Artificial Sequence
<220> FEATURE:
<223> OTHER INFORMATION: synthetic

<400> SEQUENCE: 144
tcatccgata tggtgatcca tttttaggat gggagcctga gtcaactggt tttgtaa      57

<210> SEQ ID NO 145
<211> LENGTH: 57
<212> TYPE: DNA
<213> ORGANISM: Artificial Sequence
<220> FEATURE:
<223> OTHER INFORMATION: synthetic

<400> SEQUENCE: 145
tcatccgata tggtgatcca tttttgctac atgctcttgc ttccttcatt gttcttg      57

<210> SEQ ID NO 146
<211> LENGTH: 57
<212> TYPE: DNA
<213> ORGANISM: Artificial Sequence
<220> FEATURE:
<223> OTHER INFORMATION: synthetic

<400> SEQUENCE: 146
tcatccgata tggtgatcca tttttagtgc ttatgccttt gtggttctca cagcacc      57

<210> SEQ ID NO 147
<211> LENGTH: 57
<212> TYPE: DNA
<213> ORGANISM: Artificial Sequence
<220> FEATURE:
<223> OTHER INFORMATION: synthetic

<400> SEQUENCE: 147
tcatccgata tggtgatcca tttttttgagc agttctaaac caagttcaag ttactag      57

<210> SEQ ID NO 148
<211> LENGTH: 57
<212> TYPE: DNA
<213> ORGANISM: Artificial Sequence
<220> FEATURE:
<223> OTHER INFORMATION: synthetic

<400> SEQUENCE: 148
tcatccgata tggtgatcca tttttccatg agctcagtct ctaaggcccg gtaacat      57

<210> SEQ ID NO 149
<211> LENGTH: 57
<212> TYPE: DNA
<213> ORGANISM: Artificial Sequence
<220> FEATURE:
<223> OTHER INFORMATION: synthetic

<400> SEQUENCE: 149
tcatccgata tggtgatcca tttttgactt gggttaatta gccttctagt tgaaggt    57

<210> SEQ ID NO 150
<211> LENGTH: 57
<212> TYPE: DNA
<213> ORGANISM: Artificial Sequence
<220> FEATURE:
<223> OTHER INFORMATION: synthetic

<400> SEQUENCE: 150
tcatccgata tggtgatcca tttttggagt ctgtagaaca cctttcctat ggagtct    57

<210> SEQ ID NO 151
<211> LENGTH: 57
<212> TYPE: DNA
<213> ORGANISM: Artificial Sequence
<220> FEATURE:
<223> OTHER INFORMATION: synthetic

<400> SEQUENCE: 151
tcatccgata tggtgatcca ttttttttcca cggcaccctc ctaccaaggc tcttgca    57

<210> SEQ ID NO 152
<211> LENGTH: 57
<212> TYPE: DNA
<213> ORGANISM: Artificial Sequence
<220> FEATURE:
<223> OTHER INFORMATION: synthetic

<400> SEQUENCE: 152
tcatccgata tggtgatcca tttttggcag cagcttagaa ggccaagact tagctgc    57

<210> SEQ ID NO 153
<211> LENGTH: 57
<212> TYPE: DNA
<213> ORGANISM: Artificial Sequence
<220> FEATURE:
<223> OTHER INFORMATION: synthetic

<400> SEQUENCE: 153
tcatccgata tggtgatcca tttttcttgc agtagtcaag catgacatac cctattt    57

<210> SEQ ID NO 154
<211> LENGTH: 57
<212> TYPE: DNA
<213> ORGANISM: Artificial Sequence
<220> FEATURE:
<223> OTHER INFORMATION: synthetic

<400> SEQUENCE: 154
tcatccgata tggtgatcca tttttagctg tccatgaatt tggaagtgat gtccctg    57

<210> SEQ ID NO 155
<211> LENGTH: 57
<212> TYPE: DNA
<213> ORGANISM: Artificial Sequence
<220> FEATURE:
<223> OTHER INFORMATION: synthetic

<400> SEQUENCE: 155
tcatccgata tggtgatcca tttttaagta ccatggatgt gtataggctc ctgagtc    57

```
<210> SEQ ID NO 156
<211> LENGTH: 57
<212> TYPE: DNA
<213> ORGANISM: Artificial Sequence
<220> FEATURE:
<223> OTHER INFORMATION: synthetic

<400> SEQUENCE: 156
tcatccgata tggtgatcca tttttctcc ttccctctgg cacataggta tgttcca        57

<210> SEQ ID NO 157
<211> LENGTH: 57
<212> TYPE: DNA
<213> ORGANISM: Artificial Sequence
<220> FEATURE:
<223> OTHER INFORMATION: synthetic

<400> SEQUENCE: 157
tcatccgata tggtgatcca ttttaatag tgacccaacg agatctcctg tgaaatg        57

<210> SEQ ID NO 158
<211> LENGTH: 57
<212> TYPE: DNA
<213> ORGANISM: Artificial Sequence
<220> FEATURE:
<223> OTHER INFORMATION: synthetic

<400> SEQUENCE: 158
tcatccgata tggtgatcca ttttagacc aggagagtta attaattacc tgaggac        57

<210> SEQ ID NO 159
<211> LENGTH: 57
<212> TYPE: DNA
<213> ORGANISM: Artificial Sequence
<220> FEATURE:
<223> OTHER INFORMATION: synthetic

<400> SEQUENCE: 159
tcatccgata tggtgatcca tttttgtata cttctggcct tctcaggagt aagcaga        57

<210> SEQ ID NO 160
<211> LENGTH: 57
<212> TYPE: DNA
<213> ORGANISM: Artificial Sequence
<220> FEATURE:
<223> OTHER INFORMATION: synthetic

<400> SEQUENCE: 160
tcatccgata tggtgatcca ttttaccct cgatgaggag gtttggaaag aatggat        57

<210> SEQ ID NO 161
<211> LENGTH: 57
<212> TYPE: DNA
<213> ORGANISM: Artificial Sequence
<220> FEATURE:
<223> OTHER INFORMATION: synthetic

<400> SEQUENCE: 161
tcatccgata tggtgatcca tttttgttga ctctgtactt aatgtcagaa gtggtgg       57

<210> SEQ ID NO 162
<211> LENGTH: 57
<212> TYPE: DNA
<213> ORGANISM: Artificial Sequence
<220> FEATURE:
<223> OTHER INFORMATION: synthetic
```

<400> SEQUENCE: 162
tcatccgata tggtgatcca tttttcaaag ataccacctg tcatgcaaca tatatgt     57

<210> SEQ ID NO 163
<211> LENGTH: 57
<212> TYPE: DNA
<213> ORGANISM: Artificial Sequence
<220> FEATURE:
<223> OTHER INFORMATION: synthetic

<400> SEQUENCE: 163
tcatccgata tggtgatcca tttttactgt cgtgatgtgg aactccaaaa ggtgaat     57

<210> SEQ ID NO 164
<211> LENGTH: 57
<212> TYPE: DNA
<213> ORGANISM: Artificial Sequence
<220> FEATURE:
<223> OTHER INFORMATION: synthetic

<400> SEQUENCE: 164
tcatccgata tggtgatcca tttttatgca gaatgtcatc ccttccatac ttggcag     57

<210> SEQ ID NO 165
<211> LENGTH: 57
<212> TYPE: DNA
<213> ORGANISM: Artificial Sequence
<220> FEATURE:
<223> OTHER INFORMATION: synthetic

<400> SEQUENCE: 165
tcatccgata tggtgatcca ttttttgat ttcgttacct tgaaccagtg gccaaag      57

<210> SEQ ID NO 166
<211> LENGTH: 57
<212> TYPE: DNA
<213> ORGANISM: Artificial Sequence
<220> FEATURE:
<223> OTHER INFORMATION: synthetic

<400> SEQUENCE: 166
tcatccgata tggtgatcca ttttttgac atttgtgctt taggaccata ctaggat      57

<210> SEQ ID NO 167
<211> LENGTH: 57
<212> TYPE: DNA
<213> ORGANISM: Artificial Sequence
<220> FEATURE:
<223> OTHER INFORMATION: synthetic

<400> SEQUENCE: 167
tcatccgata tggtgatcca tttttcatta aacatgagcc cttaaagcag cagttgc     57

<210> SEQ ID NO 168
<211> LENGTH: 57
<212> TYPE: DNA
<213> ORGANISM: Artificial Sequence
<220> FEATURE:
<223> OTHER INFORMATION: synthetic

<400> SEQUENCE: 168
tcatccgata tggtgatcca tttttgagca ggttatcttt attggcacaa atgttac     57

<210> SEQ ID NO 169
<211> LENGTH: 57
<212> TYPE: DNA
<213> ORGANISM: Artificial Sequence
<220> FEATURE:
<223> OTHER INFORMATION: synthetic

<400> SEQUENCE: 169
tcatccgata tggtgatcca tttttgttgc tctaggagaa ctggagtcct agcccag      57

<210> SEQ ID NO 170
<211> LENGTH: 57
<212> TYPE: DNA
<213> ORGANISM: Artificial Sequence
<220> FEATURE:
<223> OTHER INFORMATION: synthetic

<400> SEQUENCE: 170
tcatccgata tggtgatcca tttttacagg ccaaggagtt gtgacccatt agctttg      57

<210> SEQ ID NO 171
<211> LENGTH: 57
<212> TYPE: DNA
<213> ORGANISM: Artificial Sequence
<220> FEATURE:
<223> OTHER INFORMATION: synthetic

<400> SEQUENCE: 171
tcatccgata tggtgatcca tttttgtgca tggctaagtc attagcttaa ccattgc      57

<210> SEQ ID NO 172
<211> LENGTH: 57
<212> TYPE: DNA
<213> ORGANISM: Artificial Sequence
<220> FEATURE:
<223> OTHER INFORMATION: synthetic

<400> SEQUENCE: 172
tcatccgata tggtgatcca tttttgagtt cccagcagca accacaggga gggccag      57

<210> SEQ ID NO 173
<211> LENGTH: 57
<212> TYPE: DNA
<213> ORGANISM: Artificial Sequence
<220> FEATURE:
<223> OTHER INFORMATION: synthetic

<400> SEQUENCE: 173
tcatccgata tggtgatcca ttttttgtc gcatgaacat gccacatctg tccacca      57

<210> SEQ ID NO 174
<211> LENGTH: 57
<212> TYPE: DNA
<213> ORGANISM: Artificial Sequence
<220> FEATURE:
<223> OTHER INFORMATION: synthetic

<400> SEQUENCE: 174
tcatccgata tggtgatcca ttttttgaga attgtcttcc cagaagggta ggtcctt      57

<210> SEQ ID NO 175
<211> LENGTH: 70
<212> TYPE: DNA
<213> ORGANISM: Artificial Sequence
<220> FEATURE:
<223> OTHER INFORMATION: synthetic

<400> SEQUENCE: 175
tggatcacca tatcggatga tttttggcta tgtccgtaac actccttttt ggctatgtcc    60
gtaacactcc                                                          70

<210> SEQ ID NO 176
<211> LENGTH: 70
<212> TYPE: DNA
<213> ORGANISM: Artificial Sequence
<220> FEATURE:
<223> OTHER INFORMATION: synthetic

<400> SEQUENCE: 176
gaaccatggt acctgagatc tttttgaacc atggtacctg agatcttttt ggagtgttac    60
ggacatagcc                                                          70

<210> SEQ ID NO 177
<211> LENGTH: 70
<212> TYPE: DNA
<213> ORGANISM: Artificial Sequence
<220> FEATURE:
<223> OTHER INFORMATION: synthetic

<400> SEQUENCE: 177
gatctcaggt accatggttc tttttcgtcc agattatgtt ctccttttt cgtccagatt    60 atgtttctcc                                                          70

<210> SEQ ID NO 178
<211> LENGTH: 70
<212> TYPE: DNA
<213> ORGANISM: Artificial Sequence
<220> FEATURE:
<223> OTHER INFORMATION: synthetic

<400> SEQUENCE: 178
cagcttagaa tagaacattg tttttcagct tagaatagaa cattgttttt ggagaaacat    60
aatctggacg                                                          70

<210> SEQ ID NO 179
<211> LENGTH: 70
<212> TYPE: DNA
<213> ORGANISM: Artificial Sequence
<220> FEATURE:
<223> OTHER INFORMATION: synthetic

<400> SEQUENCE: 179
caatgttcta ttctaagctg tttttctgga tgatgttctc tcatctttt ctggatgatg    60 ttctctcatc                                                          70

<210> SEQ ID NO 180
<211> LENGTH: 70
<212> TYPE: DNA
<213> ORGANISM: Artificial Sequence
<220> FEATURE:
<223> OTHER INFORMATION: synthetic

<400> SEQUENCE: 180
gctcaagtgt tggtgaaggt tttttgctca agtgttggtg aaggtttttt gatgagagaa    60
catcatccag                                                          70

```
<210> SEQ ID NO 181
<211> LENGTH: 70
<212> TYPE: DNA
<213> ORGANISM: Artificial Sequence
<220> FEATURE:
<223> OTHER INFORMATION: synthetic

<400> SEQUENCE: 181
accttcacca acacttgagc tttttatagc cctggacatg aacgtttttt atagccctgg    60
acatgaacgt                                                          70

<210> SEQ ID NO 182
<211> LENGTH: 70
<212> TYPE: DNA
<213> ORGANISM: Artificial Sequence
<220> FEATURE:
<223> OTHER INFORMATION: synthetic

<400> SEQUENCE: 182
cgtacagagg tagcaaggga tttttcgtac agaggtagca agggattttt acgttcatgt    60
ccagggctat                                                          70

<210> SEQ ID NO 183
<211> LENGTH: 70
<212> TYPE: DNA
<213> ORGANISM: Artificial Sequence
<220> FEATURE:
<223> OTHER INFORMATION: synthetic

<400> SEQUENCE: 183
tcccttgcta cctctgtacg tttttcgatg catcaggtac ccagtttttt cgatgcatca    60
ggtacccagt                                                          70

<210> SEQ ID NO 184
<211> LENGTH: 70
<212> TYPE: DNA
<213> ORGANISM: Artificial Sequence
<220> FEATURE:
<223> OTHER INFORMATION: synthetic

<400> SEQUENCE: 184
tggatcacca tatcggatga tttttggcta tgtccgtaac actccttttt ggctatgtcc    60
gtaacactcc                                                          70

<210> SEQ ID NO 185
<211> LENGTH: 70
<212> TYPE: DNA
<213> ORGANISM: Artificial Sequence
<220> FEATURE:
<223> OTHER INFORMATION: synthetic

<400> SEQUENCE: 185
gaaccatggt acctgagatc tttttgaacc atggtacctg agatcttttt ggagtgttac    60
ggacatagcc                                                          70

<210> SEQ ID NO 186
<211> LENGTH: 70
<212> TYPE: DNA
<213> ORGANISM: Artificial Sequence
<220> FEATURE:
<223> OTHER INFORMATION: synthetic
```

<400> SEQUENCE: 186
gatctcaggt accatggttc tttttcgtcc agattatgtt tctccttttt cgtccagatt   60
atgtttctcc                                                          70

<210> SEQ ID NO 187
<211> LENGTH: 70
<212> TYPE: DNA
<213> ORGANISM: Artificial Sequence
<220> FEATURE:
<223> OTHER INFORMATION: synthetic

<400> SEQUENCE: 187
cagcttagaa tagaacattg tttttcagct tagaatagaa cattgttttt ggagaaacat   60
aatctggacg                                                          70

<210> SEQ ID NO 188
<211> LENGTH: 70
<212> TYPE: DNA
<213> ORGANISM: Artificial Sequence
<220> FEATURE:
<223> OTHER INFORMATION: synthetic

<400> SEQUENCE: 188
caatgttcta ttctaagctg tttttctgga tgatgttctc tcatcttttt ctggatgatg   60
ttctctcatc                                                          70

<210> SEQ ID NO 189
<211> LENGTH: 70
<212> TYPE: DNA
<213> ORGANISM: Artificial Sequence
<220> FEATURE:
<223> OTHER INFORMATION: synthetic

<400> SEQUENCE: 189
gctcaagtgt tggtgaaggt tttttgctca agtgttggtg aaggtttttt gatgagagaa   60
catcatccag                                                          70

<210> SEQ ID NO 190
<211> LENGTH: 70
<212> TYPE: DNA
<213> ORGANISM: Artificial Sequence
<220> FEATURE:
<223> OTHER INFORMATION: synthetic

<400> SEQUENCE: 190
accttcacca acacttgagc tttttatagc cctggacatg aacgtttttt atagccctgg   60
acatgaacgt                                                          70

<210> SEQ ID NO 191
<211> LENGTH: 70
<212> TYPE: DNA
<213> ORGANISM: Artificial Sequence
<220> FEATURE:
<223> OTHER INFORMATION: synthetic

<400> SEQUENCE: 191
cgtacagagg tagcaaggga tttttcgtac agaggtagca agggatttt acgttcatgt    60 ccagggctat                                                          70

```
<210> SEQ ID NO 192
<211> LENGTH: 70
<212> TYPE: DNA
<213> ORGANISM: Artificial Sequence
<220> FEATURE:
<223> OTHER INFORMATION: synthetic

<400> SEQUENCE: 192
tcccttgcta cctctgtacg tttttcgatg catcaggtac ccagttttttt cgatgcatca    60 ggtacccagt                                                           70

<210> SEQ ID NO 193
<211> LENGTH: 70
<212> TYPE: DNA
<213> ORGANISM: Artificial Sequence
<220> FEATURE:
<223> OTHER INFORMATION: synthetic

<400> SEQUENCE: 193
gatggtcgta gtgtggcaca tttttgatgg tcgtagtgtg gcacattttt actgggtacc    60
tgatgcatcg                                                           70

<210> SEQ ID NO 194
<211> LENGTH: 70
<212> TYPE: DNA
<213> ORGANISM: Artificial Sequence
<220> FEATURE:
<223> OTHER INFORMATION: synthetic

<400> SEQUENCE: 194
tgtgccacac tacgaccatc tttttatgag tcttccagtc gtagtttttt atgagtcttc    60
cagtcgtagt                                                           70

<210> SEQ ID NO 195
<211> LENGTH: 70
<212> TYPE: DNA
<213> ORGANISM: Artificial Sequence
<220> FEATURE:
<223> OTHER INFORMATION: synthetic

<400> SEQUENCE: 195
tcacgtaatg ttctccacga tttttcacg taatgttctc cacgattttt actacgactg     60
gaagactcat                                                           70

<210> SEQ ID NO 196
<211> LENGTH: 70
<212> TYPE: DNA
<213> ORGANISM: Artificial Sequence
<220> FEATURE:
<223> OTHER INFORMATION: synthetic

<400> SEQUENCE: 196
tcgtggagaa cattacgtga tttttcttgc tatcttccag cgaagttttt cttgctatct    60
tccagcgaag                                                           70

<210> SEQ ID NO 197
<211> LENGTH: 70
<212> TYPE: DNA
<213> ORGANISM: Artificial Sequence
<220> FEATURE:
<223> OTHER INFORMATION: synthetic
```

```
<400> SEQUENCE: 197
tagttgaagg agtgctcgtg ttttttagtt gaaggagtgc tcgtgttttt cttcgctgga    60
agatagcaag                                                           70

<210> SEQ ID NO 198
<211> LENGTH: 70
<212> TYPE: DNA
<213> ORGANISM: Artificial Sequence
<220> FEATURE:
<223> OTHER INFORMATION: synthetic

<400> SEQUENCE: 198
cacgagcact ccttcaacta ttttcacttt cgtcatggag catgattttt cacttcgtca    60
tggagcatga                                                           70

<210> SEQ ID NO 199
<211> LENGTH: 20
<212> TYPE: DNA
<213> ORGANISM: Artificial Sequence
<220> FEATURE:
<223> OTHER INFORMATION: synthetic

<400> SEQUENCE: 199
tcatgctcca tgacgaagtg                                                20

<210> SEQ ID NO 200
<211> LENGTH: 70
<212> TYPE: DNA
<213> ORGANISM: Artificial Sequence
<220> FEATURE:
<223> OTHER INFORMATION: synthetic

<400> SEQUENCE: 200
ccgcagacat ctgtaaagac tttttccgat gttgacggac taatcttttt ccgatgttga    60
cggactaatc                                                           70

<210> SEQ ID NO 201
<211> LENGTH: 70
<212> TYPE: DNA
<213> ORGANISM: Artificial Sequence
<220> FEATURE:
<223> OTHER INFORMATION: synthetic

<400> SEQUENCE: 201
tagtagttca gacgccgtta ttttttagta gttcagacgc cgttattttt gattagtccg    60
tcaacatcgg                                                           70

<210> SEQ ID NO 202
<211> LENGTH: 70
<212> TYPE: DNA
<213> ORGANISM: Artificial Sequence
<220> FEATURE:
<223> OTHER INFORMATION: synthetic

<400> SEQUENCE: 202
taacggcgtc tgaactacta tttttccgta cctagataca ctcaattttt ccgtacctag    60
atacactcaa                                                           70

<210> SEQ ID NO 203
<211> LENGTH: 70
<212> TYPE: DNA
<213> ORGANISM: Artificial Sequence
```

<220> FEATURE:
<223> OTHER INFORMATION: synthetic

<400> SEQUENCE: 203
ccaggcaata tggtggtaca tttttccagg caatatggtg gtacatttttt ttgagtgtat    60 ctaggtacgg                                                            70

<210> SEQ ID NO 204
<211> LENGTH: 70
<212> TYPE: DNA
<213> ORGANISM: Artificial Sequence
<220> FEATURE:
<223> OTHER INFORMATION: synthetic

<400> SEQUENCE: 204
tgtaccacca tattgcctgg tttttcgtga agcttgagtg gaatctttttt cgtgaagctt    60 gagtggaatc                                                            70

<210> SEQ ID NO 205
<211> LENGTH: 70
<212> TYPE: DNA
<213> ORGANISM: Artificial Sequence
<220> FEATURE:
<223> OTHER INFORMATION: synthetic

<400> SEQUENCE: 205
gtgtgaggcg ctagagcata tttttgtgtg aggcgctaga gcatattttt gattccactc    60
aagcttcacg                                                            70

<210> SEQ ID NO 206
<211> LENGTH: 70
<212> TYPE: DNA
<213> ORGANISM: Artificial Sequence
<220> FEATURE:
<223> OTHER INFORMATION: synthetic

<400> SEQUENCE: 206
tatgctctag cgcctcacac tttttggtat ggcacgccta atctgttttt ggtatggcac    60
gcctaatctg                                                            70

<210> SEQ ID NO 207
<211> LENGTH: 70
<212> TYPE: DNA
<213> ORGANISM: Artificial Sequence
<220> FEATURE:
<223> OTHER INFORMATION: synthetic

<400> SEQUENCE: 207
atctccagtg gcatccttct tttttatctc cagtggcatc cttcttttt cagattaggc     60 gtgccatacc                                                            70

<210> SEQ ID NO 208
<211> LENGTH: 70
<212> TYPE: DNA
<213> ORGANISM: Artificial Sequence
<220> FEATURE:
<223> OTHER INFORMATION: synthetic

<400> SEQUENCE: 208
agaaggatgc cactggagat tttttggtaa ctgcgcatag ttggcttttt ggtaactgcg    60
catagttggc                                                            70

```
<210> SEQ ID NO 209
<211> LENGTH: 70
<212> TYPE: DNA
<213> ORGANISM: Artificial Sequence
<220> FEATURE:
<223> OTHER INFORMATION: synthetic

<400> SEQUENCE: 209
ggtacagtaa gtgagaatcc tttttggtac agtaagtgag aatcctttt gccaactatg    60 cgcagttacc                                                          70

<210> SEQ ID NO 210
<211> LENGTH: 70
<212> TYPE: DNA
<213> ORGANISM: Artificial Sequence
<220> FEATURE:
<223> OTHER INFORMATION: synthetic

<400> SEQUENCE: 210
ggattctcac ttactgtacc tttttgccac cttaacacgc gatgattttt gccaccttaa    60
cacgcgatga                                                          70

<210> SEQ ID NO 211
<211> LENGTH: 70
<212> TYPE: DNA
<213> ORGANISM: Artificial Sequence
<220> FEATURE:
<223> OTHER INFORMATION: synthetic

<400> SEQUENCE: 211
cattgatctt ggtgctgctg tttttcattg atcttggtgc tgctgttttt tcatcgcgtg    60
ttaaggtggc                                                          70

<210> SEQ ID NO 212
<211> LENGTH: 70
<212> TYPE: DNA
<213> ORGANISM: Artificial Sequence
<220> FEATURE:
<223> OTHER INFORMATION: synthetic

<400> SEQUENCE: 212
cagcagcacc aagatcaatg tttttgctat tacgagcgct tggattttt gctattacga    60 gcgcttggat                                                          70

<210> SEQ ID NO 213
<211> LENGTH: 70
<212> TYPE: DNA
<213> ORGANISM: Artificial Sequence
<220> FEATURE:
<223> OTHER INFORMATION: synthetic

<400> SEQUENCE: 213
tatgttgtgc cttacgcctc ttttttatgt tgtgccttac gcctcttttt atccaagcgc    60
tcgtaatagc                                                          70

<210> SEQ ID NO 214
<211> LENGTH: 70
<212> TYPE: DNA
<213> ORGANISM: Artificial Sequence
<220> FEATURE:
<223> OTHER INFORMATION: synthetic
```

-continued

<400> SEQUENCE: 214
gaggcgtaag gcacaacata ttttttaac cgaactgacg gccattttt ttaaccgaac    60 tgacggccat                                                         70

<210> SEQ ID NO 215
<211> LENGTH: 20
<212> TYPE: DNA
<213> ORGANISM: Artificial Sequence
<220> FEATURE:
<223> OTHER INFORMATION: synthetic

<400> SEQUENCE: 215
atggccgtca gttcggttaa                                              20

<210> SEQ ID NO 216
<211> LENGTH: 70
<212> TYPE: DNA
<213> ORGANISM: Artificial Sequence
<220> FEATURE:
<223> OTHER INFORMATION: synthetic

<400> SEQUENCE: 216
tggatcacca tatcggatga tttttggcta tgtccgtaac actccttttt ggctatgtcc    60
gtaacactcc                                                         70

<210> SEQ ID NO 217
<211> LENGTH: 70
<212> TYPE: DNA
<213> ORGANISM: Artificial Sequence
<220> FEATURE:
<223> OTHER INFORMATION: synthetic

<400> SEQUENCE: 217
tcatccgata tggtgatcca tttttcatc cgatatggtg atccattttt ggagtgttac    60
ggacatagcc                                                         70

<210> SEQ ID NO 218
<211> LENGTH: 70
<212> TYPE: DNA
<213> ORGANISM: Artificial Sequence
<220> FEATURE:
<223> OTHER INFORMATION: synthetic

<400> SEQUENCE: 218
ccgcagacat ctgtaaagac tttttccgat gttgacggac taatctttt ccgatgttga    60 cggactaatc                                                         70

<210> SEQ ID NO 219
<211> LENGTH: 70
<212> TYPE: DNA
<213> ORGANISM: Artificial Sequence
<220> FEATURE:
<223> OTHER INFORMATION: synthetic

<400> SEQUENCE: 219
gtctttacag atgtctgcgg ttttgtctt tacagatgtc tgcggttttt gattagtccg    60
tcaacatcgg                                                         70

CONSECUTIVE HYBRIDIZATION FOR MULTIPLEXED ANALYSIS OF BIOLOGICAL SAMPLES

CROSS-REFERENCE TO RELATED APPLICATIONS

This application represents the national stage entry of PCT International Application No. PCT/US2017/029271, filed on Apr. 25, 2017, and claims the benefit of U.S. Provisional Patent Application No. 62/334,047, filed on May 10, 2016, which is incorporated by reference in its entirety as if fully set forth herein.

STATEMENT REGARDING FEDERALLY SPONSORED RESEARCH

Not applicable.

BACKGROUND

The ability to profile genome and transcriptome comprehensively in single cells in situ is crucial to understand the molecular mechanisms underlying cancer, neurobiology, and stem cell biology. Due to the inherent heterogeneity of these biological systems, conventional genomic technologies carried out on pools of cells mask gene expression variations and spatial complexity of different RNA species in a population. The differences between individual cells in complex biological systems may have significant consequences in the function and health of the entire systems. Thus, single cell analysis is required to explore such cell heterogeneity. The precise location of cells in a tissue and transcripts in a cell is critical for effective cell-cell interactions and gene expression regulation, which determine cell fates and functions. Therefore, to fully understand the organization, regulation and function of a heterogeneous biological system, the in situ analysis of the transcriptome of individual cells in the system is required. However, most of the existing methods for in situ RNA analysis can only quantify a small number of different transcripts in a biological sample. Other in situ sequencing based methods may miss transcripts present at low copy numbers. For example, single molecule fluorescence in situ hybridization (smFISH) has emerged as a powerful tool to quantify the copy number and spatial organization of transcripts in single cells, but only a handful of different RNA species in a biological sample can be simultaneously detected using smFISH. Although such technologies significantly advanced our ability to analyze transcripts in their natural contexts, many problems remain. For example, the multiplexing capacities of most current approaches are insufficient to permit transcriptome-wide analysis, methods involving time-consuming photobleaching processes to remove fluorescence signals are limited by the small number of cells analyzed in a sample, and the cost of preparing multiple FISH probes, which must be synthesized individually, can be prohibitively expensive.

Accordingly, there remains a need in the art for improved methods for single-cell in situ genetic analysis. In particular, there remains a need for single-cell in situ genetic analysis methods that are comprehensive, low cost, and high-throughput that yield high quality data with single-molecule sensitivity.

SUMMARY

The present disclosure overcomes the aforementioned drawbacks by providing low-cost, high-throughput, rapid and high-quality methods of consecutive in situ hybridization capable of in situ analysis of genome and transcriptome in individual cells of intact tissues with single-molecule sensitivity. In this method, individual genomic loci or transcripts are visualized as single fluorescent spots, which remain in place during consecutive hybridization. In each cycle of consecutive hybridization, detectably labeled probes hybridize to the probe used in the previous cycle, and also introduce the binding sites for the probe of the following cycle. Through consecutive cycles of probe hybridization, imaging, and detectable signal removal, different genomic loci or RNA species can be identified (e.g., as fluorescent spots) with unique color sequences or other detectable signal profiles. The number of varied color sequences increases exponentially with the number of hybridization cycles, which enables the genome or transcriptome-wide analysis.

In a first aspect, provided herein is a method of in situ analysis of transcripts or DNA loci in a single cell. The method can comprise or consist essentially of the following steps: (a) performing a first contacting step that comprises contacting a cell comprising a plurality of transcripts or genomic loci to a plurality of pre-decoding oligonucleotides, where each pre-decoding oligonucleotide of the plurality comprises a targeting sequence that specifically hybridizes to a target transcript or genomic locus and further comprises one or more binding sites for specific hybridization to a decoding oligonucleotide in a subsequent hybridization step, wherein the first contacting step occurs under conditions that promote hybridization of the plurality of pre-decoding oligonucleotides to target transcripts or genomic loci; (b) performing a second contacting step that comprises contacting the cell with a plurality of decoding oligonucleotides, wherein each decoding oligonucleotide comprises a detectable moiety and is configured to have one or more binding sites for specific hybridization to a pre-decoding oligonucleotide, wherein the second contacting step occurs under conditions that promote hybridization of the decoding oligonucleotides to the pre-decoding oligonucleotides; and (c) imaging the cell after the second contacting step whereby a detectable signal generated from hybridization of the decoding oligonucleotides to the pre-decoding oligonucleotides, whereby the detectable signal indicates hybridization to the target transcript or genomic locus. In some cases, the method further comprises (d) removing the detectable signal generated in step (c); and (e) optionally consecutively repeating the first and second contacting steps, imaging step, and removing step, each time with a new plurality of detectably labeled decoding oligonucleotides configured to have one or more binding sites for hybridization to detectably labeled decoding oligonucleotides of each subsequent cycle, wherein each new plurality of differs from detectably labeled decoding oligonucleotides of each subsequent cycle by at least one difference in detectable moiety labeling. Steps (a)-(e) can be consecutively performed at least 16 times. Two decoding probes can be used to detect each target transcript or genomic locus.

The detectable moiety can be selected from the group consisting of a fluorophore, radioactive isotope, and metal isotope. The fluorophore can be selected from the group consisting of TAMRA, ALEXA FLUOR™ 594, ATTO 647N, and ATTO 700. In some cases, the first plurality of oligonucleotides targets at least 10 different transcripts and/or DNA loci. Removing the detectable signal can comprise chemically cleaving the detectable moiety.

In some cases, the method further comprises washing to remove unhybridized oligonucleotides and non-specifically hybridized oligonucleotides following each contacting step.

In another aspect, provided herein is a kit for detecting target transcripts or DNA loci in a cell sample. The kit can comprise or consist essentially of a first plurality of oligonucleotide probes configured to hybridize to a target transcript or DNA locus; a second plurality of oligonucleotide probes, which second plurality includes oligonucleotides labeled with a detectable moiety and configured to have one or more binding sites for specific hybridization to oligonucleotides of the first plurality; and a written insert component comprising instructions for performing consecutive in situ analysis of target transcripts or DNA loci according to a method provided herein. The detectable moiety can be selected from the group consisting of a fluorophore, radioactive isotope, and metal isotope. The oligonucleotide probes can be synthetic DNA oligonucleotide probes.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figures 1A, 1B, 1C:
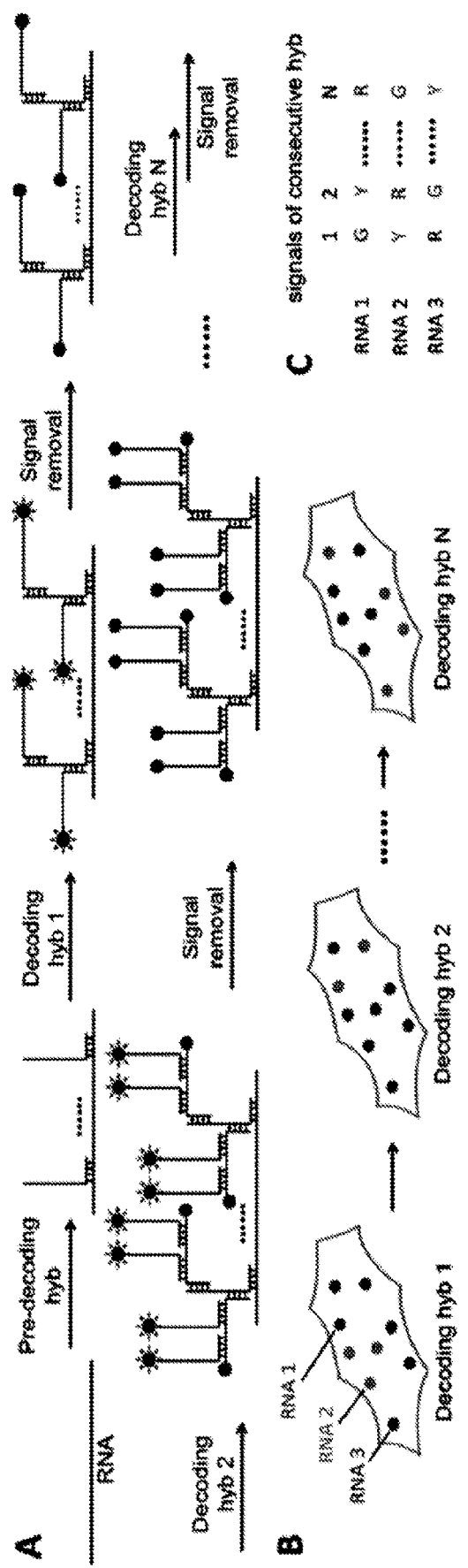
FIGS. 1A-1C illustrate an exemplary protocol for single-cell in situ transcriptome analysis having single-molecule sensitivity. (A) Schematic diagram of consecutive cycles of probe hybridization, fluorescence imaging, and signal removal. (B) Schematic diagram of C-FISH images. In each cycle, individual transcript is visualized as a single spot with a specific color. (C) As transcripts remain in place during the whole C-FISH cycles, different RNA species can be distinguished by the unique color sequences.

The present invention, in some embodiments thereof, relates to methods for high throughput transcriptome and genome analysis using consecutive fluorescence in situ hybridization (C-FISH) and probes specifically designed thereof. The methods and compositions provided herein are based at least in part on the inventors' discovery of a low-cost, high-throughput, and high-quality approach to consecutive fluorescence in situ hybridization (C-FISH). As described herein, the inventors' discovery provides for in situ analysis of transcriptome in individual cells of intact tissues with single-molecule sensitivity. Accordingly, in a first aspect, provided herein is a method for analysis of transcripts or genomic (e.g., DNA) loci in a single cell. In exemplary embodiments, the method comprises (a) performing a first contacting step that comprises contacting a cell comprising a plurality of transcripts or genomic loci to a plurality of pre-decoding oligonucleotides, where each pre-decoding oligonucleotide of the plurality comprises a targeting sequence that specifically hybridizes to a target transcript or genomic locus and further comprises one or more binding sites for specific hybridization to a decoding oligonucleotide in a subsequent hybridization step, wherein the first contacting step occurs under conditions that promote hybridization of the plurality of pre-decoding oligonucleotides to target transcripts or genomic loci; (b) performing a second contacting step that comprises contacting the cell with a plurality of decoding oligonucleotides, wherein each decoding oligonucleotide comprises a detectable moiety and is configured to have one or more binding sites for specific hybridization to a pre-decoding oligonucleotide, wherein the second contacting step occurs under conditions that promote hybridization of the decoding oligonucleotides to the pre-decoding oligonucleotides; and (c) imaging the cell after the second contacting step whereby a detectable signal generated from hybridization of the decoding oligonucleotides to the pre-decoding oligonucleotides, whereby the detectable signal indicates hybridization to the target transcript or genomic locus. In some cases, the method further comprises (d) removing the detectable signal generated in step (c); and (e) optionally consecutively repeating the first and second contacting steps, imaging step, and removing step, each time with a new plurality of detectably labeled decoding oligonucleotides configured to have one or more binding sites for hybridization to detectably labeled decoding oligonucleotides of each subsequent cycle, wherein each new plurality of differs from detectably labeled decoding oligonucleotides of each subsequent cycle by at least one difference in detectable moiety labeling.

As described herein, the methods of the present invention provide for visualization and analysis of individual transcripts as single fluorescent spots. When the contacted cell is fixed using a fixative such as paraformaldehyde or formaldehyde, the fluorescent spots remain in place during each consecutive hybridization cycle. For each cycle, fluorescently labeled decoding probes specifically hybridize to the probe used in the previous cycle (e.g., unlabeled pre-decoding probes or previously contacted plurality of decoding probes) and, in doing so, also introduce binding sites for probes of the following cycle. Through consecutive cycles of probe hybridization, fluorescence imaging, and signal removal, different RNA species can be identified as fluorescent spots with unique color sequences. The number of varied color sequences increases exponentially with the number of hybridization cycles, which enables genome-wide or transcriptome-wide analysis.

Referring to FIG. 1, a de novo approach for single-cell in situ transcriptome analysis is presented. As shown in FIG. 1A, each transcript is hybridized with a set of pre-decoding probes. Preferably, the pre-decoding probes are not labeled with a detectable moiety. The pre-decoding probes have varied targeting sequences to bind to the different regions on the target transcript. In addition, the pre-decoding probes all share a common decoding sequence for specific hybridization to decoding probes. Subsequently, a plurality of detectably labeled decoding probes is contacted to the cell under conditions suitable for hybridization of detectable decoding probes to transcript-bound pre-decoding probes. As a result, an individual transcript can be visualized as a single spot when visualized using, for example, fluorescence microscope (FIG. 1B) to detect decoding probes comprising a fluorescent moiety. After detection of the detectable moiety by any appropriate means (e.g., fluorescence microscopy) and data storage, the detectable moiety is removed.

To maintain the signal to background ratio in subsequent consecutive cycles, each plurality of decoding probes is configured to have one or more binding sites to hybridize to the probe of the previous cycle (either the pre-decoding probes or the decoding probes of a previous hybridization/visualization/removal cycle). Each plurality of decoding probes is further configured to have multiple binding sites for hybridization to the probe of the following cycle. As cells or tissue samples are fixed, transcripts remain in place during the whole C-FISH process. Through consecutive cycles of probe hybridization, fluorescence imaging, and signal removal, each transcript is identified as a fluorescent spot with a unique color sequence (FIG. 1C).

The terms "hybridize" and "hybridization" as used herein refer to the association of two nucleic acids to form a stable duplex. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.). One of skill in the art will understand that "hybridization" as used herein does not require a precise base-for-base complementarity. That is, a duplex can form, between two nucleic acids that contained mismatched base pairs. The conditions under which nucleic acids that are perfectly complementary or that contain mismatched base pairs will hybridize to form a duplex are well known in the art and are described, for example, in MOLECULAR CLONING: A LABORATORY MANUAL, 3rd ed., Sambrook et al., eds., Cold Spring Harbor Press, Cold Spring Harbor (2001) at Chapter 10, which is herein incorporated by reference. As used herein, the term "complementary" refers to a nucleic acid that forms a stable duplex with its "complement". For example, nucleotide sequences that are complementary to each other have mismatches at less than 20% of the bases, at less than about 10% of the bases, preferably at less than about 5% of the bases, and more preferably have no mismatches.

As used herein, the term "probe" refers to and encompasses any physical string or collection of monomer units (e.g., nucleotides) that can connect to form a string of nucleotides, including a polymer of nucleotides (e.g., DNA oligonucleotides, RNA oligonucleotides, peptide nucleic acid (PNA) oligonucleotides, locked nucleic acid (LNA) oligonucleotides), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the oligonucleotide can be deoxyribonucleotides, ribonucleotides or nucleotide analogs, and can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The oligonucleotide can additionally comprise non-nucleotide elements such as labels, quenchers, blocking groups, or the like. The oligonucleotide can be single-stranded or double-stranded.

As used herein, the terms "target nucleic acid" and "target transcript" include nucleic acids originating from one or more biological entities within a sample. The target nucleic acid of interest to be detected in a sample can be a sequence or a subsequence from DNA, such as nuclear or mitochondrial DNA, or cDNA that is reverse transcribed from RNA in the sample. In some cases, the target transcript is a RNA sequence of interest, such as mRNA, rRNA, tRNA, miRNA, siRNAs, antisense RNAs, or long noncoding RNAs. More generally, the target transcripts and target nucleic acids sequences of interest can be selected from any combination of sequences or subsequences in the genome (e.g., a genomic locus or genomic loci) or transcriptome of a species or an environment. In some cases, a defined set of decoding probes are designed to hybridize to the plurality of sequences that would be expected in a sample, for example a genome or transcriptome, or a smaller set when the sequences are known and well-characterized, such as from an artificial source.

Oligonucleotide probes useful for the methods provided herein are of any length sufficient to permit probe penetration and to optimize hybridization of probes of subsequent C-FISH. Preferably, probe length is about 20 bases to about 500 bases. As probe length increases, so increases the number of binding sites that can be incorporated into a given probe for hybridization to the probe of the following cycle as well as the signal to noise ratio. However, longer than 500 bases, the probes may not efficiently penetrate the cellular membrane. The C-FISH hybridization oligonucleotide probes provided herein include probes consisting of between 20 and 500 nucleotides, 20 and 250, 50 and 250, 150 and 250 nucleotides, 20 and 150, or 50 and 150 nucleotides, inclusive.

Any detectable moiety can be used for the methods provided herein. As used herein, "detectable moiety" refers to a label molecule (isotopic or non-isotopic) possessing a property or function which can be used for detection purposes and include, without limitation, chromophore moieties, fluorescent moieties, phosphorescent moieties, chemiluminescent moieties, light absorbing moieties, radioactive isotopes, metal isotopes, and particle-based signals. Suitable fluorescent moieties are those known from the art of immunofluorescence technologies, e.g., flow cytometry or fluorescence microscopy. In some cases, the detectable moiety is a fluorophore. In other cases, the detectable moiety is a radioactive isotope (e.g., $^{13}C$, $^{15}N$) or metal isotope. Metal isotopes can detected by mass spectrometry imaging. Several methods are well described in the literature and are known to be used to render signals that are detectable by various means (e.g., microscopy (bright-field, fluorescent, electron, scanning probe)), flow cytometry (fluorescent, particle, magnetic) or a scanning device.

Fluorophores that can be used for attachment to oligonucleotides post-synthesis include, without limitation, TAMRA (labeled with tetramethylrhodamine or "TMR"), ALEXA FLUOR™ 594, and ATTO 647N and ATTO 700 fluorophores (ATTO-TEC, Germany). Other fluorophores appropriate for use according to the methods provided herein include, without limitation, ALEXA FLUOR™ 350, ALEXA FLUOR™ 532, ALEXA FLUOR™ 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7. In addition to the use of fluorophores as a detectable moiety, other luminescent labels such as chemiluminescent agents can be used.

When fluorescently labeled oligonucleotides are used, fluorescence photomicroscopy can be used to detect and record the results of consecutive in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular Probes) for a review of methods for painting chromosomes and detecting painted chromosomes.

Any appropriate means of removing a detectable signal or detectable moiety (e.g., a fluorophore) can be used according to the methods provided herein. Methods of removal can include without limitation photobleaching (see Example 1 below), chemical deactivation, chemical cleavage of the fluorophores (e.g., disulfide cleavage), enzymatic cleavage (using, for example, an exonuclease, endonuclease, protease, or USER™ (Uracil-Specific Excision Reagent) cleavage system), DNA/RNA strand displacement, chemical or heat denaturing of an intermediate fluorescent oligonucleotide, and the like. Removal of fluorescence can be performed by photobleaching or by chemical removal of the fluorescent moiety (or other detectable moiety). Since photobleaching can be a time-consuming step, in some cases the methods provided herein comprise efficiently removing fluorescence signals by chemical deactivation or chemical or enzymatic cleavage of detectable moieties from decoding probes. After hybridization with cleavable fluorescent decoding probes, all of the different fluorophores in the whole sample can be chemically cleaved simultaneously in 30 minutes. To further reduce the assay time by decreasing the cycle numbers and increasing the number of fluorophores used in each cycle, C-FISH probes can be synthesized to be labeled with various cleavable fluorophores. Consequently, C-FISH performed with such cleavable fluorescent probes reduces the cycling time (minus imaging) from weeks to approximately 1.5-2.5 hours for thousands of single cells in a human tissue.

Using the reaction scheme set forth in FIG. 5A, NHS ester-functionalized cleavable fluorescent probes can be obtained comprising TAMRA (labeled with tetramethylrhodamine or "TMR"), ALEXA FLUOR™ 594, ATTO 647N (ATTO-TEC, Germany), and ATTO 700 fluorophores (ATTO-TEC, Germany). C-FISH probes comprising TAMRA, ALEXA FLUOR™ 594, ATTO 647N, and ATTO 700 can be imaged using filter sets SP102v1 (Chroma), a custom set5 (Omega), SP104v2 (Chroma) and SP105 (Chroma), respectively. With C-FISH probes labeled with these four fluorophores (TAMRA, ALEXA FLUOR™ 594, ATTO 647N, and ATTO 700), only 5 cycles ($4^5=1,024$) are required to analyze one thousand RNA species.

In some cases, the methods provided herein comprise chemical inactivation of fluorophores. For example, fluorophores can be inactivated by oxidation. Protocols for oxidation of dyes with hydrogen peroxide, which can be catalyzed using either acidic or basic conditions, or reactive oxygen species (ROS) are known to those practitioners in the art for changing the fluorescent properties of dyes and fluorescent proteins.

To minimize issues of autofluorescence or background signal, cleavable fluorescent decoding probes can be designed to include three or more probe binding sites. Thus, an increased number of probes will hybridize to each transcript to enhance signal to noise ratio. As used herein, the terms "binding," "to bind," "binds," "bound," or any derivation thereof refers to any stable, rather than transient, chemical bond between two or more molecules, including, but not limited to, covalent bonding, ionic bonding, and hydrogen bonding. Thus, this term also encompasses interaction between a nucleic acid molecule and another entity such as, a nucleic acid or probe element. Specifically, binding, in certain embodiments, includes the hybridization of nucleic acids.

Biological samples can be obtained from any biological entity containing genetic material (e.g., nucleic acid). Sources for nucleic acid-containing biological entities include, without limitation, an organism or organisms including a cell or cells, bacteria, yeast, fungi, algae, viruses, and mammals (e.g., humans) or other animal species. The methods and compositions described herein can be performed using a variety of biological or clinical samples comprising cells that are in any (or all) stage(s) of the cell cycle (e.g., mitosis, meiosis, interphase, G0, G1, S and/or G2). As used herein, the term "sample" include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. These examples are not to be construed as limiting the sample types applicable to the methods and/or compositions described herein. Samples are prepared for assays of the invention using conventional techniques, which typically depend on the source from which a sample or specimen is taken. Preferably, the methods provided herein comprise a cell fixation step. For example, the cells of a biological sample (e.g., tissue sample) can be fixed (e.g., using formaldehyde or paraformaldehyde fixation techniques known to one of ordinary skill in the art). Any fixative that does not affect DNA or RNA can be utilized in according to the methods provided herein.

Kits

In another aspect, provided herein is a kit comprising reagents for performing in situ analysis of transcripts or DNA loci according to a method provided herein. In some cases, the kit comprises a first plurality of oligonucleotide probes configured to hybridize to a target transcript or DNA locus; a second plurality of oligonucleotide probes, which second plurality includes oligonucleotides labeled with a detectable moiety and configured to have one or more binding sites for specific hybridization to oligonucleotides of the first plurality; and a written insert component comprising instructions for performing consecutive in situ analysis of target transcripts or DNA loci according to a method provided herein. Preferably, the detectable moiety is a fluorophore. As described herein, the oligonucleotide probes can be synthetic DNA oligonucleotide probes. A kit will preferably include instructions for employing the kit components as well the use of any other reagent not included in the kit. Instructions may include variations that can be implemented.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

As used herein, "about" means within 5% of a stated concentration range or within 5% of a stated time frame.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials & Methods

Preparation of Fluorescently Labeled Oligonucleotide Probes:

Oligonucleotides (1 nmol) were dissolved in 1 μL of nuclease-free water. To this solution was added the sodium bicarbonate aqueous solution (1M, 3 μL) and Quasar 570 (BioSearch) or Cy5 (AAT Bioquest) in DMF (20 mM, 5 μL). The mixture was then diluted to a volume of 10 μL with nuclease-free water and incubated at RT for 2 hours. Subsequently, the fluorescently labeled oligonucleotides were purified by nucleotide removal kit (Qiagen) and dried in a Savant SpeedVac Concentrator (Thermo Scientific).

Cell Culture:

HeLa CCL-2 cells (ATCC) were maintained in Dulbelcco's modified Eagle's Medium (DMEM) supplemented with 10% fetal bovine serum, 10 U/mL penicillin and 100 g/mL streptomycin in a humidified atmosphere at 37° C. with 5% CO2. Cells were plated on chambered coverglass (Thermo Scientific) and allowed to reach 60% confluency in 1-2 days.

Cell Fixation:

Cultured HeLa CCL-2 cells were washed with 1×PBS at RT for 5 minutes, fixed with fixation solution (4% formaldehyde (Polysciences) in 1×PBS) at RT for 10 minutes, and subsequently washed another 2 times with 1×PBS at RT, each for 5 minutes.

The dried fluorophore conjugated oligonucleotides were then further purified via an HPLC (Agilent) equipped with a C18 column (Agilent) and a dual wavelength detector set to detect DNA absorption (260 nm) as well as the absorption of the coupled fluorophore (548 nm for Quasar 570, 650 nm for Cy5). For the gradient, triethyl ammonium acetate (Buffer A) (0.1 M, pH 6.5) and acetonitrile (Buffer B) (pH 6.5) were used, ranging from 7% to 30% Buffer B over the course of 30 minutes, then at 70% Buffer B for 10 minutes followed with 7% Buffer B for another 10 minutes, all at a flow rate of 1 mL per minute. The collected fraction was subsequently dried in a Savant SpeedVac Concentrator and stored as the stock decoding probe solution at 4° C. in 200 μL nuclease-free water to which 1× Tris EDTA (TE) (2 μL, pH 8.0) was added.

Consecutive RNA FISH:

The pre-decoding hybridization solution was prepared by dissolving 10 pmol of GAPDH and Ki67 pre-decoding probes in 100 μL of pre-decoding hybridization buffer (100 mg/mL dextran sulfate, 1 mg/mL *Escherichia coli* tRNA, 2 mM vanadyl ribonucleoside complex, 20 μg/mL bovine serum albumin and 10% formamide in 2×SSC). The decoding hybridization solution was prepared by adding 2 μL of the Quasar 570 or Cy5 labeled stock decoding probe solution to 100 μL of decoding hybridization buffer (100 mg/mL dextran sulfate, 2 mM vanadyl ribonucleoside complex, and 10% formamide in 2×SSC).

The fixed HeLa CCL-2 cells were first permeabilized with 70% (v/v) EtOH at 4° C. for at least overnight, and then washed once by wash buffer (10% formamide in 2×SSC) for 5 minutes. Subsequently, the cells were incubated with pre-decoding hybridization solution at 37° C. overnight, and washed 3 times with wash buffer, each at 37° C. for 30 minutes. Then, the cells were incubated with decoding hybridization solution at 37° C. for 30 minutes, and then with 5 ng/mL DAPI in wash buffer at 37° C. for 30 minutes. After incubated with GLOX buffer (0.4% glucose and 10 mM Tris HCl in 2×SSC) for 1-2 min, the stained cells were imaged in GLOX solution (0.37 mg/mL glucose oxidase and 1% catalase in GLOX buffer). After imaging, each target cell in 1×PBS was photobleached individually with the Quasar 570 filter for 20 s or the Cy5 filter for 5 s at each z step. 1×PBS was changed every 3 minutes during photobleaching to remove the radicals. Following photobleaching, the HeLa cells were imaged again in GLOX solution, and then incubated with the next cycle decoding hybridization solution.

Consecutive DNA FISH:

The fixed HeLa CCL-2 cells were incubated with 0.5% (v/v) Triton-X100 in 1×PBS at RT for 10 minutes, and then with 0.1% Tween-20 in 1×PBS at RT for 2 min. After incubated with 0.1 M HCl at RT for 5 min, the cells were washed three times with 2×SSCT (0.3 M NaCl, 0.03 M Sodium Citrate, 0.1% Tween-20) at RT for 2 minutes. The cells were incubated with 70% formamide in 2×SSCT at RT for 5 min, then at 78° C. for 15 minutes, and then at 60° C. for 20 minutes. Subsequently, the cells were incubated with 100 μL of predecoding hybridization solution composed of 80 pmol of the decoding probes, 2×SSCT, 50% formamide and 10% dextran sulfate (wt/vol) at 78° C. for 5 minutes. After hybridized at 37° C. overnight, the cells were washed in 2×SSCT at 60° C. for 15 minutes, then in 2×SSCT at RT for 10 min, and then for 10 min in 0.2×SSC at RT. Subsequently, the cells were incubated with 100 μL of decoding hybridization solution composed of 2 μL of the Quasar 570 or Cy5 labeled stock decoding probe solution, 2×SSCT, 10% formamide and 10% dextran sulfate (wt/vol) at 37° C. for 30 minutes. The cells were washed with 10% formamide in 2×SSCT at 37° C. for 30 minutes, and then with 5 ng/mL DAPI and 10% formamide in 2×SSCT at 37° C. for 30 minutes. After washed with GLOX buffer for 1-2 min at TR, the cells were imaged in GLOX solution. After imaging, each target cell in 1×PBS was photobleached individually with the Quasar 570 filter for 20 seconds or the Cy5 filter for 5 seconds at each z step. 1×PBS was changed every 3 minutes during photobleaching to remove the radicals. Following photobleaching, the HeLa cells were imaged again in GLOX solution, and then incubated with the next cycle decoding hybridization solution.

Imaging and Data Analysis:

Stained cells were imaged under a Nikon Ti-E epifluorescence microscope equipped with 100× objective, using a 5-μm z range and 0.3-μm z pacing. Images were captured using a CoolSNAP HQ2 camera and NIS-Elements Imaging software. Chroma filters 49004 and 49009 were used for Quasar 570 and Cy5, respectively.

Example 1: Single-Cell In Situ Transcript Analysis by C-FISH

Figures 2A, 2B, 2C:
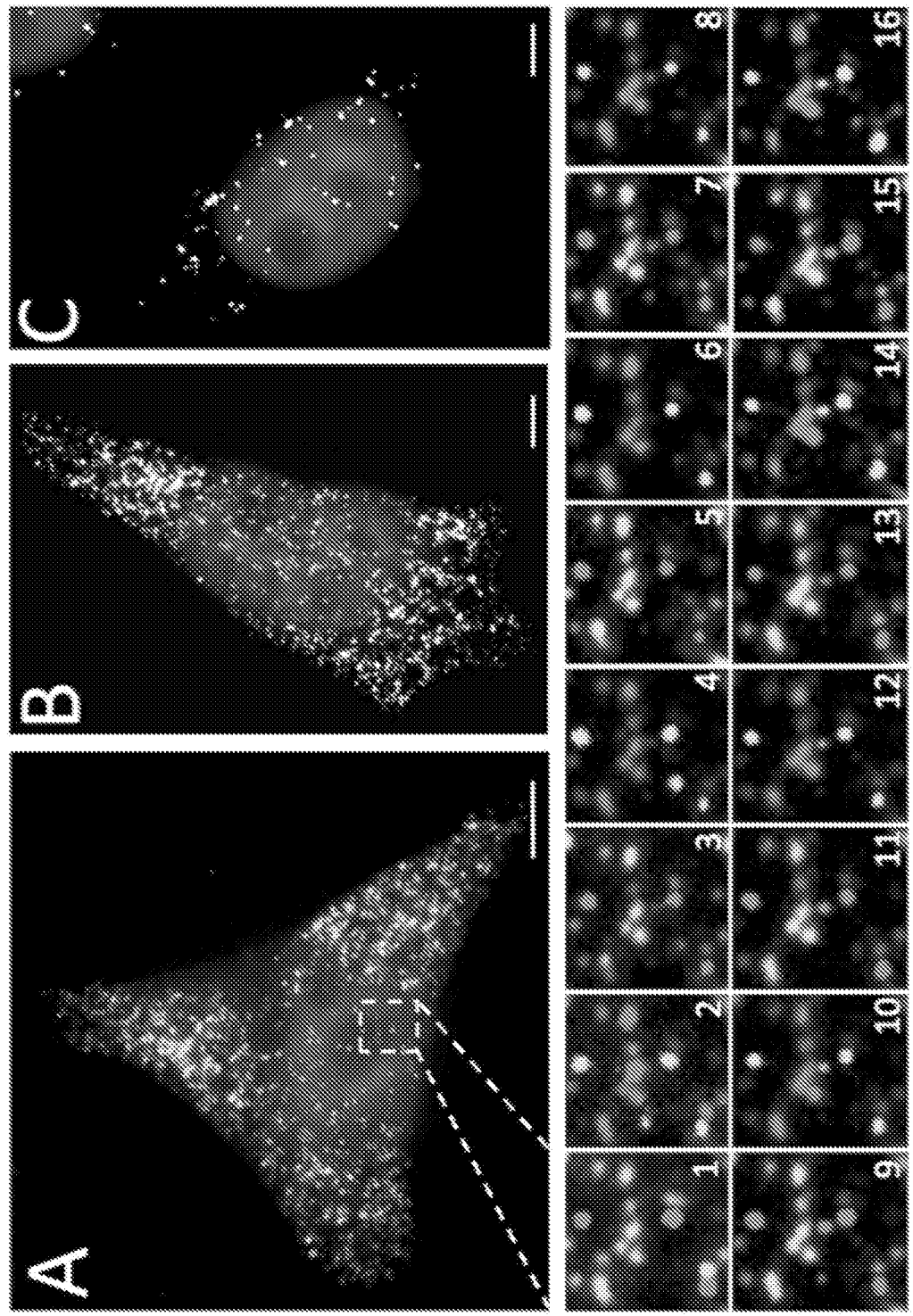
FIGS. 2A-2C demonstrate single-cell in situ transcript analysis by C-FISH. (A) In the first cycle of C-FISH, GAPDH and Ki67 transcripts are detected as green and red spots, respectively. Through 16 cycles of C-FISH, individual transcripts are detected as fluorescent spots with unique color sequences (inset panels 1-16). (B) GAPDH and (C) Ki67 transcripts are detected by conventional smFISH. Scale bars, 5 μm.
Figures 3A, 3B:
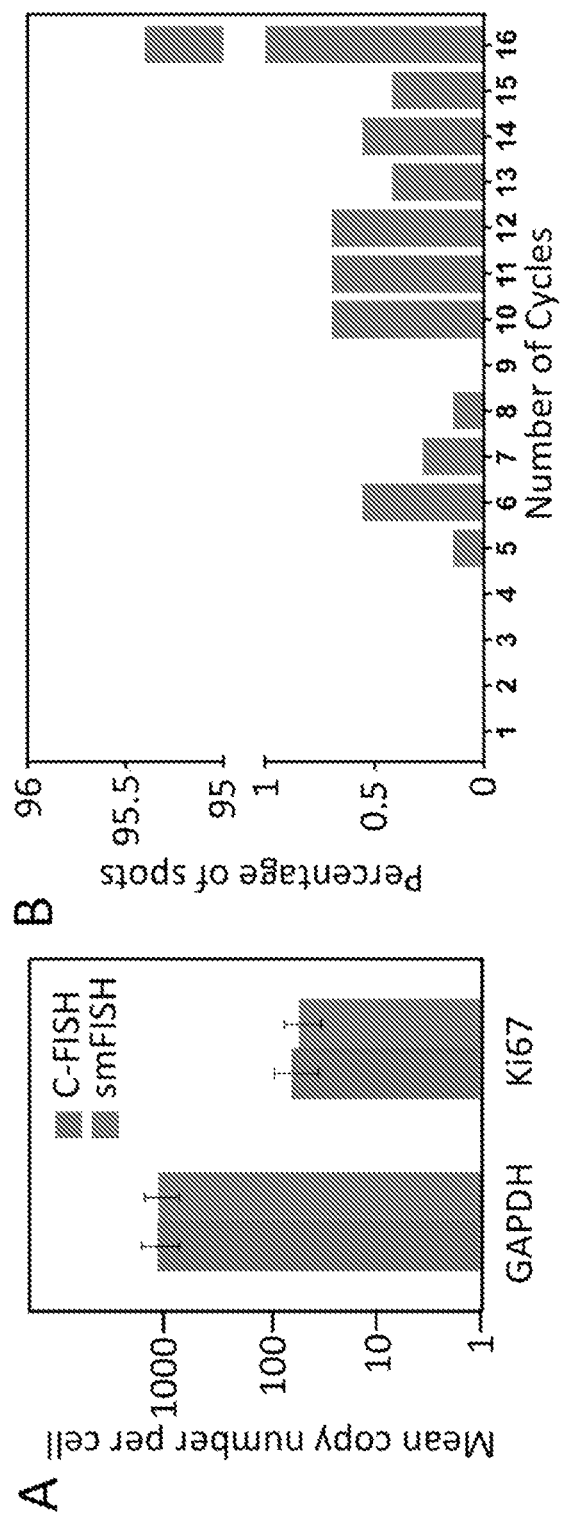
FIGS. 3A-3B. (A) Mean copy number per cell (n=30 cells) of GAPDH and Ki67 transcripts measured by C-FISH and smFISH. The y axis is on a logarithmic scale. (B) Percentage of spots accurately identified in C-FISH cycles.

To demonstrate the feasibility of applying C-FISH for single-cell in situ transcriptome analysis, we designed and synthesized pre-decoding probes and corresponding decoding probes for mRNA GAPDH and Ki67. The mRNA binding sequences on the pre-decoding probes were generated by using the well documented software[5] for RNA FISH probe design. And the binding sequences on decoding probes were selected from a set of orthogonal sequences, which have been established to minimize cross-hybridization[15]. We synthesized the pre-coding probes with natural nucleotides and amino modified decoding probes on a DNA synthesizer. Subsequently, the amino groups on the decoding probes were coupled to NHS ester modified Quasar 570 or Cy5. In each C-FISH cycle, two decoding probes labeled with different fluorophores were applied to stain GAPDH and Ki67 transcripts, respectively (FIG. 2A, top). Through 16 cycles of hybridization, imaging, and photobleaching, individual GAPDH and Ki67 transcripts were unambiguously detected as fluorescent spots with distinct color sequences (FIG. 2A, bottom). The copy numbers and spatial distributions of transcripts obtained by C-FISH are consistent with those in conventional smFISH (FIGS. 2B and 2C). The copy numbers per cell obtained by C—FISH and conventional smFISH closely resembled each other (FIG. 3A). Additionally, more than 95% of the spots identified by colocalization in the first two C-FISH cycles reoccurred throughout all the following 14 cycles (FIG. 3B). All the reappearing spots could be accurately and unambiguously identified by comparing the signal intensities in different fluorescence channels. These results suggest that the time-consuming error correction process in sequential hybridization and MER-FISH can be completely removed; and the entire transcriptome can be quantified by C-FISH using the $2^{16}=65,536$ distinct color sequences at the single-molecule sensitivity.

Example 2: Single-Cell In Situ Genomic Loci Analysis by C-FISH

Figure 4:
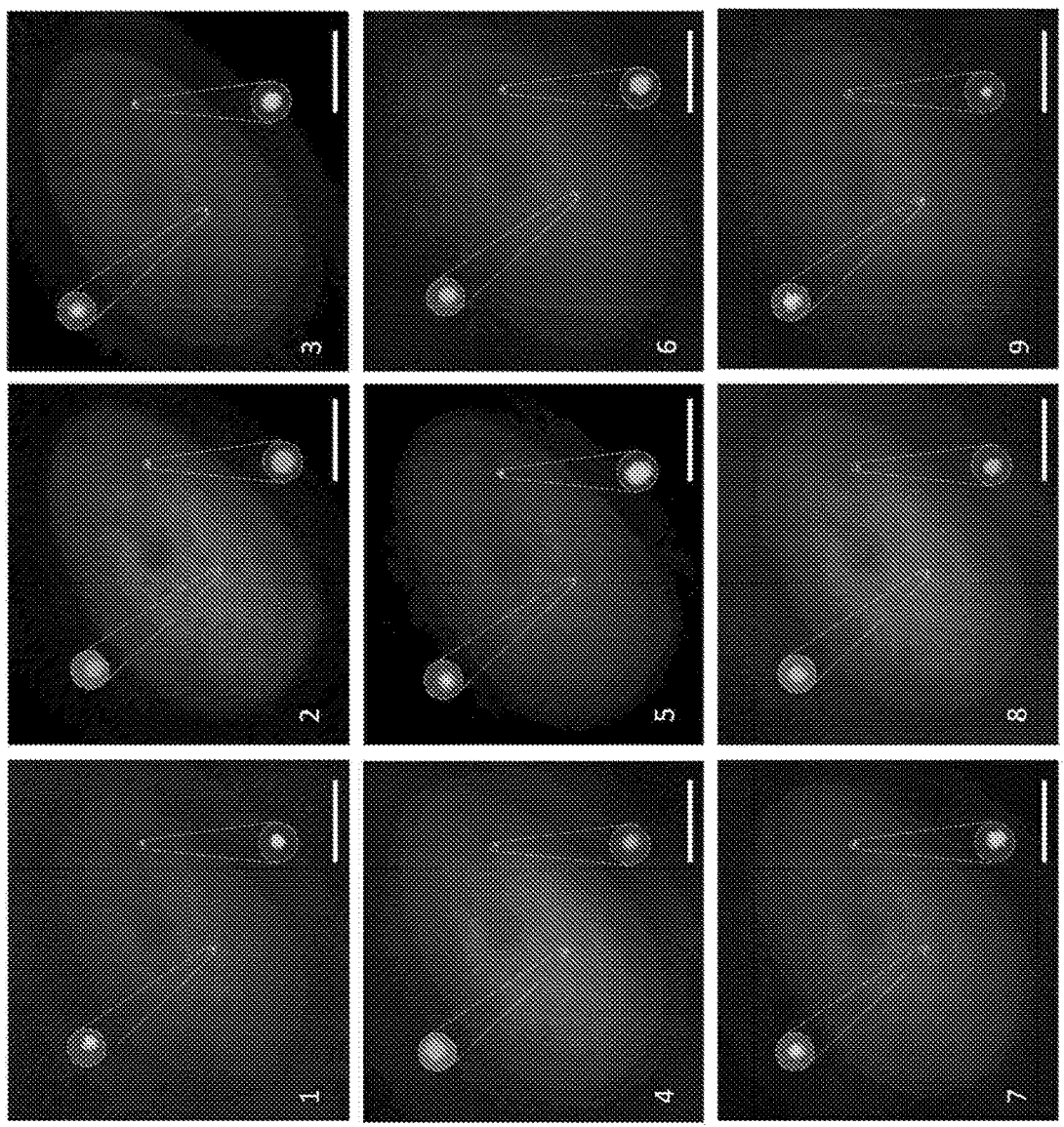
FIG. 4 is a series of images (panels 1-9) collected for single-cell in situ genomic loci analysis by C-FISH. Through 9 cycles of C-FISH, genomic locus 4p16.1 is detected as fluorescent spots with unique color sequences. Scale bars, 5 μm.

To demonstrate the feasibility of applying C-FISH for single-cell in situ genome analysis, we designed and prepared 100 pre-decoding probes targeting human 4p16.1. The pre-decoding probes for DNA C-FISH (Table 3) were designed and synthesized similarly as the ones for RNA C-FISH (see Table 1 and Table 2). For each DNA or RNA C-FISH cycle, two orthogonal decoding probes labeled with Quasar 570 or Cy5 (Tables 4 and 5) were incubated with HeLa cells. Only one of two probes has complimentary binding sequences to the probes used in the previous cycle. As shown in FIG. 4, nine cycles of hybridization, imaging, and photobleaching were performed to unambiguously detect individual genomic loci 4p16.1 as fluorescent spots with a unique color sequence.

TABLE 1

RNA C-FISH Pre-decoding Probes (5'-3')

| GAPDH (5'-3') | SEQ ID NO: |
|---|---|
| tcatccgatatggtgatccattttttcatccgatatggtgatccattttttaacggctgcccattcattt | 1 |
| tcatccgatatggtgatccattttttcatccgatatggtgatccattttttggagaaatcgggccagctag | 2 |

TABLE 1-continued

RNA C-FISH Pre-decoding Probes (5'-3')

| GAPDH (5'-3') | SEQ ID NO: |
|---|---|
| tcatccgatatggtgatccatttttctcatccgatatggtgatccatttttctaggaaaagcatcacccg | 3 |
| tcatccgatatggtgatccatttttctcatccgatatggtgatccatttttcccaatacgaccaaatcaga | 4 |
| tcatccgatatggtgatccatttttctcatccgatatggtgatccatttttcagagttaaaagcagccctg | 5 |
| tcatccgatatggtgatccatttttctcatccgatatggtgatccatttttgggtcattgatggcaacaat | 6 |
| tcatccgatatggtgatccatttttctcatccgatatggtgatccatttttaccatgtagttgaggtcaat | 7 |
| tcatccgatatggtgatccatttttctcatccgatatggtgatccatttttcatgggtggaatcatattgg | 8 |
| tcatccgatatggtgatccatttttctcatccgatatggtgatccattttttgacggtgccatggaattt | 9 |
| tcatccgatatggtgatccatttttctcatccgatatggtgatccatttttcattgatgacaagcttcccg | 10 |
| tcatccgatatggtgatccatttttctcatccgatatggtgatccatttttctggaagatggtgatgggat | 11 |
| tcatccgatatggtgatccatttttctcatccgatatggtgatccatttttcttgattttggagggatctc | 12 |
| tcatccgatatggtgatccatttttctcatccgatatggtgatccatttttcagtggactccacgacgtac | 13 |
| tcatccgatatggtgatccatttttctcatccgatatggtgatccattttttctccatggtggtgaagac | 14 |
| tcatccgatatggtgatccatttttctcatccgatatggtgatccatttttagagatgatgacccttttgg | 15 |
| tcatccgatatggtgatccatttttctcatccgatatggtgatccatttttatgacgaacatgggggcatc | 16 |
| tcatccgatatggtgatccatttttctcatccgatatggtgatccatttttgtcatacttctcatggttca | 17 |
| tcatccgatatggtgatccatttttctcatccgatatggtgatccatttttattgctgatgatcttgaggc | 18 |
| tcatccgatatggtgatccatttttctcatccgatatggtgatccatttttctaagcagttggtggtgcag | 19 |
| tcatccgatatggtgatccatttttctcatccgatatggtgatccatttttagttgtcatggatgaccttg | 20 |
| tcatccgatatggtgatccatttttctcatccgatatggtgatccatttttcatgagtccttccacgatac | 21 |
| tcatccgatatggtgatccatttttctcatccgatatggtgatccatttttcagtgatggcatggactgtg | 22 |
| tcatccgatatggtgatccatttttctcatccgatatggtgatccattttttagaggcagggatgatgttc | 23 |
| tcatccgatatggtgatccatttttctcatccgatatggtgatccattttttcagctcagggatgaccttg | 24 |
| tcatccgatatggtgatccatttttctcatccgatatggtgatccatttttcactgacacgttggcagtgg | 25 |
| tcatccgatatggtgatccatttttctcatccgatatggtgatccattttttttggcaggttttctagacg | 26 |
| tcatccgatatggtgatccatttttctcatccgatatggtgatccatttttcaccttcttgatgtcatcat | 27 |
| tcatccgatatggtgatccatttttctcatccgatatggtgatccatttttgctgttgaagtcagaggaga | 28 |
| tcatccgatatggtgatccatttttctcatccgatatggtgatccatttttcgtcaaaggtggaggagtgg | 29 |
| tcatccgatatggtgatccatttttctcatccgatatggtgatccattttttaaagtggtcgttgagggcaa | 30 |
| tcatccgatatggtgatccatttttctcatccgatatggtgatccattttttgtcataccaggaaatgagct | 31 |
| tcatccgatatggtgatccatttttctcatccgatatggtgatccattttttgttgctgtagccaaattcg | 32 |
| tcatccgatatggtgatccatttttctcatccgatatggtgatccatttttcagtgagggtctctctcttc | 33 |
| tcatccgatatggtgatccatttttctcatccgatatggtgatccattttttaactgtgaggaggggagatt | 34 |
| tcatccgatatggtgatccatttttctcatccgatatggtgatccatttttctcttcaagggtctacatg | 35 |
| tcatccgatatggtgatccatttttctcatccgatatggtgatccattttttatggtacatgacaaggtgcg | 36 |
| tcatccgatatggtgatccatttttctcatccgatatggtgatccattttttttaactggttgagcacaggg | 37 |

TABLE 2

RNA C-FISH Pre-decoding Probes (5'-3')

| Ki67 (5'-3') | SEQ ID NO: |
|---|---|
| gtctttacagatgtctgcggttttttgtctttacagatgtctgcggtttttttgcattaccagagactttct | 38 |
| gtctttacagatgtctgcggttttttgtctttacagatgtctgcggttttttggcttataaccaagctttgt | 39 |
| gtctttacagatgtctgcggttttttgtctttacagatgtctgcggttttttggagttttcctaggactag | 40 |
| gtctttacagatgtctgcggttttttgtctttacagatgtctgcggttttttaggaacctctgtctgagat | 41 |
| gtctttacagatgtctgcggttttttgtctttacagatgtctgcggtttttagacactctctttgaaggca | 42 |
| gtctttacagatgtctgcggttttttgtctttacagatgtctgcggtttttgttcattgacctttgaggac | 43 |
| gtctttacagatgtctgcggttttttgtctttacagatgtctgcggtttttcgtggcctgtactaaattga | 44 |
| gtctttacagatgtctgcggttttttgtctttacagatgtctgcggtttttagttgttgagcactctgtag | 45 |
| gtctttacagatgtctgcggttttttgtctttacagatgtctgcggttttttctaatacactgccgtctta | 46 |
| gtctttacagatgtctgcggttttttgtctttacagatgtctgcggttttttgtttgcagtggatactgtt | 47 |
| gtctttacagatgtctgcggttttttgtctttacagatgtctgcggtttttgtagcttctgtatattcctg | 48 |
| gtctttacagatgtctgcggttttttgtctttacagatgtctgcggtttttcgtgtctttcatgagttctg | 49 |
| gtctttacagatgtctgcggttttttgtctttacagatgtctgcggtttttctggttgtaatgactggcag | 50 |
| gtctttacagatgtctgcggttttttgtctttacagatgtctgcggttttttcatcagtcattgattcctc | 51 |
| gtctttacagatgtctgcggttttttgtctttacagatgtctgcggtttttttcctgatacttctcttgg | 52 |
| gtctttacagatgtctgcggttttttgtctttacagatgtctgcggtttttctgatggcattagattcctg | 53 |
| gtctttacagatgtctgcggttttttgtctttacagatgtctgcggtttttcttcacctactgatggttta | 54 |
| gtctttacagatgtctgcggttttttgtctttacagatgtctgcggtttttctgagacttctcttggactg | 55 |
| gtctttacagatgtctgcggttttttgtctttacagatgtctgcggttttttcctgagtgcgaagaattct | 56 |
| gtctttacagatgtctgcggttttttgtctttacagatgtctgcggtttttcgttagtcattgattcctc | 57 |
| gtctttacagatgtctgcggttttttgtctttacagatgtctgcggttttttgtgacttggtgtctggaag | 58 |
| gtctttacagatgtctgcggttttttgtctttacagatgtctgcggtttttagctctgtaggatactttgg | 59 |
| gtctttacagatgtctgcggttttttgtctttacagatgtctgcggtttttgtgttgatgtctttctcttc | 60 |
| gtctttacagatgtctgcggttttttgtctttacagatgtctgcggttttttctattgctgccaggtaaat | 61 |
| gtctttacagatgtctgcggttttttgtctttacagatgtctgcggttttttttccttacgagtttgtagc | 62 |
| gtctttacagatgtctgcggttttttgtctttacagatgtctgcggttttttggtgtctggaaaagctctc | 63 |
| gtctttacagatgtctgcggttttttgtctttacagatgtctgcggtttttgattgcggagatttgcaga | 64 |
| gtctttacagatgtctgcggttttttgtctttacagatgtctgcggtttttgtgttgatgtctttctcttc | 65 |
| gtctttacagatgtctgcggttttttgtctttacagatgtctgcggtttttgtgattttgtcatcggtcat | 66 |
| gtctttacagatgtctgcggttttttgtctttacagatgtctgcggtttttaggatatcttgagtcgttgc | 67 |
| gtctttacagatgtctgcggttttttgtctttacagatgtctgcggtttttctggaagagctctttcaagc | 68 |
| gtctttacagatgtctgcggttttttgtctttacagatgtctgcggtttttctgagacttctcttggactg | 69 |
| gtctttacagatgtctgcggttttttgtctttacagatgtctgcggtttttctactgatggtgttcgtttc | 70 |
| gtctttacagatgtctgcggttttttgtctttacagatgtctgcggttttttcatcagtcattgattcctc | 71 |
| gtctttacagatgtctgcggttttttgtctttacagatgtctgcggtttttccttaaacgctttgatgctc | 72 |
| gtctttacagatgtctgcggttttttgtctttacagatgtctgcggtttttgcacgttgcttcaatacttt | 73 |
| gtctttacagatgtctgcggttttttgtctttacagatgtctgcggttttttttgcagattccttcaatgc | 74 |

TABLE 3

DNA C-FISH Pre-decoding Probes

5'→3'

5'-tcatccgatatggtgatccattttttctgttccttgctccttgctttctccatactc (SEQ ID NO: 75)

5'-tcatccgatatggtgatccattttttcttgaacaccttttccaactcaccgtgctggt (SEQ ID NO: 76)

5'-tcatccgatatggtgatccattttttggcattctcttcaaacctccaggtattgtgta (SEQ ID NO: 77)

5'-tcatccgatatggtgatccattttttgttacagcataagatagaccgtaaaagccaac (SEQ ID NO: 78)

5'-tcatccgatatggtgatccattttttcccagaagtcattgctaaagcaggaaggccca (SEQ ID NO: 79)

5'-tcatccgatatggtgatccattttttatgatggcaatcctggatgagtgttttagtct (SEQ ID NO: 80)

5'-tcatccgatatggtgatccattttttctgccattagctgtgggtcgatcgtgtccta (SEQ ID NO: 81)

5'-tcatccgatatggtgatccattttttagtgtcccagatagcagagaggctagtgtga (SEQ ID NO: 82)

5'-tcatccgatatggtgatccattttttactgagtgtgagtttccagcccagggtgctgg (SEQ ID NO: 83)

5'-tcatccgatatggtgatccattttttctcaagagccctattcatgggagtggactctt (SEQ ID NO: 84)

5'-tcatccgatatggtgatccattttttctgcagagcccaagataagagatggccctgag (SEQ ID NO: 85)

5'-tcatccgatatggtgatccattttttgtcatactgtgcctaatgaatcactggatata (SEQ ID NO: 86)

5'-tcatccgatatggtgatccattttttagctcaacccaggagaaggatttgttcttgga (SEQ ID NO: 87)

5'-tcatccgatatggtgatccattttttttatagggagtcctgactattcttgttctgt (SEQ ID NO: 88)

5'-tcatccgatatggtgatccattttttccttcagtcttcaactcttgatacctgttaat (SEQ ID NO: 89)

5'-tcatccgatatggtgatccattttttataaacataggcatgctcaagttaagtgcct (SEQ ID NO: 90)

5'-tcatccgatatggtgatccattttttagggttcaaacttggtggtgtccaggtagcta (SEQ ID NO: 91)

5'-tcatccgatatggtgatccattttttacaaagcacctaattgggaaacacatggctct (SEQ ID NO: 92)

5'-tcatccgatatggtgatccattttttaatagcttcagaagacagtaatgcagcatgag (SEQ ID NO: 93)

5'-tcatccgatatggtgatccattttttcttagcacattggttactgaggaccagaaggt (SEQ ID NO: 94)

5'-tcatccgatatggtgatccattttttgcagggaactaatacagtattacctgctttga (SEQ ID NO: 95)

5'-tcatccgatatggtgatccattttttcttaatgcaggaagttgtacaaatgcctcca (SEQ ID NO: 96)

5'-tcatccgatatggtgatccattttttgtgctgtaacctctcaccatgtttaaggttgc (SEQ ID NO: 97)

5'-tcatccgatatggtgatccattttttcatatttgacctgaatcttagaacctagcca (SEQ ID NO: 98)

5'-tcatccgatatggtgatccattttttcaaaccaatcataggaaagcagcagtgcagt (SEQ ID NO: 99)

5'-tcatccgatatggtgatccattttttcattaggtggctgagtccaaaatgtcctcatc (SEQ ID NO: 100)

5'-tcatccgatatggtgatccattttttaggaagtatgtatgttgggagcttctgggctc (SEQ ID NO: 101)

5'-tcatccgatatggtgatccattttttccaggacagctgtgccagaactgccctgtgtg (SEQ ID NO: 102)

5'-tcatccgatatggtgatccattttttggtgtcattatgtgtcggttttctcaactata (SEQ ID NO: 103)

5'-tcatccgatatggtgatccattttttggattgtccatattatcatccatctgttaggt (SEQ ID NO: 104)

5'-tcatccgatatggtgatccattttttgggtttcaaatgattcacaagttttccagtca (SEQ ID NO: 105)

5'-tcatccgatatggtgatccattttttgttagcatgaggaatcagatacaaggtttga (SEQ ID NO: 106)

5'-tcatccgatatggtgatccattttttactgtgtgtaaattacaggagggaccttaaat (SEQ ID NO: 107)

5'-tcatccgatatggtgatccattttttgagagctggtaatacaaggtagccagaggtct (SEQ ID NO: 108)

5'-tcatccgatatggtgatccattttttcgactagattcaaacatgtttcctttccttgg (SEQ ID NO: 109)

5'-tcatccgatatggtgatccattttttagtcacatgtgatactgtgtattagtgatggg (SEQ ID NO: 110)

5'-tcatccgatatggtgatccattttttgactgccctggtgaatgtgagatgtctggac (SEQ ID NO: 111)

5'-tcatccgatatggtgatccattttttgcagctcagagtggcctttgacagcataaagc (SEQ ID NO: 112)

TABLE 3-continued

DNA C-FISH Pre-decoding Probes

5'→3'

5'-tcatccgatatggtgatccattttttgcgtatgactgacatcacttccatcattttgg (SEQ ID NO: 113)

5'-tcatccgatatggtgatccattttttgtggtgtcagtacttctggcagtggctatgtg (SEQ ID NO: 114)

5'-tcatccgatatggtgatccattttttgcttgtgtgcagggatgacttaaaggaagtct (SEQ ID NO: 115)

5'-tcatccgatatggtgatccattttttgcctgtgactaagatgaaggtaccttcttagc (SEQ ID NO: 116)

5'-tcatccgatatggtgatccattttttgtgggaaacattcctcacctggatcatcctt (SEQ ID NO: 117)

5'-tcatccgatatggtgatccattttttcttgagtccaatgcccaacacatcagatctgg (SEQ ID NO: 118)

5'-tcatccgatatggtgatccattttttggctctctccaaatgatagtttgtaagatgtc (SEQ ID NO: 119)

5'-tcatccgatatggtgatccattttttgctgttagtgtctgcagtgggaaatggtgac (SEQ ID NO: 120)

5'-tcatccgatatggtgatccattttttcaatgttgccctagtgtctatatagaccttgc (SEQ ID NO: 121)

5'-tcatccgatatggtgatccattttttgtgtggtaaagggccgggtattgggaagctga (SEQ ID NO: 122)

5'-tcatccgatatggtgatccattttttctgacttctcagctctgagcaaggcatttcag (SEQ ID NO: 123)

5'-tcatccgatatggtgatccattttttcctgcagaatctgaaacttgagcatttacctg (SEQ ID NO: 124)

5'-tcatccgatatggtgatccattttttatcctcaggtttcaaatgacatacatgatgga (SEQ ID NO: 125)

5'-tcatccgatatggtgatccattttttgccagcttggtcagaaagtttcagcttcatat (SEQ ID NO: 126)

5'-tcatccgatatggtgatccattttttggatgcttcattgtaagaggcctgtcctgtg (SEQ ID NO: 127)

5'-tcatccgatatggtgatccattttttgttcttctagatgtctgtggcactccctgag (SEQ ID NO: 128)

5'-tcatccgatatggtgatccattttttaaatgtctacacatcctgtcttccctgaggag (SEQ ID NO: 129)

5'-tcatccgatatggtgatccattttttaggtatgtcttgggtcactttacagactggat (SEQ ID NO: 130)

5'-tcatccgatatggtgatccattttttcttctccatgatgttcaaatgggagaataaac (SEQ ID NO: 131)

5'-tcatccgatatggtgatccattttttgaaatctaatttcctcaaggtagctcctaggg (SEQ ID NO: 132)

5'-tcatccgatatggtgatccattttttgctgtcttcacttttgaagaattcttgaccac (SEQ ID NO: 133)

5'-tcatccgatatggtgatccatttttttgtgatacagcttgcaactccacaccctggt (SEQ ID NO: 134)

5'-tcatccgatatggtgatccattttttcaggacattgtactgcaggaattggaatctga (SEQ ID NO: 135)

5'-tcatccgatatggtgatccatttttttgtaggttcctctatgtgctgcttttccaga (SEQ ID NO: 136)

5'-tcatccgatatggtgatccattttttgatcttctaatcacctcccagggtctggctgg (SEQ ID NO: 137)

5'-tcatccgatatggtgatccattttttctaatgcacgtgactaatccttagactgctta (SEQ ID NO: 138)

5'-tcatccgatatggtgatccattttttgatgaccaagtgggattgaacttctgtccggt (SEQ ID NO: 139)

5'-tcatccgatatggtgatccatttttttcaatgacttcttagggtacccttgaaggagc (SEQ ID NO: 140)

5'-tcatccgatatggtgatccattttttcacagcagtccatattcagttagctctcatat (SEQ ID NO: 141)

5'-tcatccgatatggtgatccatttttttccatctgtaaactaggatgagtagttttccc (SEQ ID NO: 142)

5'-tcatccgatatggtgatccattttttggtttgagctgataagacatagaagtactaca (SEQ ID NO: 143)

5'-tcatccgatatggtgatccattttttaggatgggagcctgagtcaactggttttgtaa (SEQ ID NO: 144)

5'-tcatccgatatggtgatccattttttgctacatgctcttgcttccttcattgttcttg (SEQ ID NO: 145)

5'-tcatccgatatggtgatccattttttagtgcttatgcctttgtggttctcacagcacc (SEQ ID NO: 146)

5'-tcatccgatatggtgatccattttttgagcagttctaaaccaagttcaagttactag (SEQ ID NO: 147)

5'-tcatccgatatggtgatccattttttccatgagctcagtctctaaggcccggtaacat (SEQ ID NO: 148)

5'-tcatccgatatggtgatccattttttgacttgggttaattagccttctagttgaaggt (SEQ ID NO: 149)

5'-tcatccgatatggtgatccattttttggagtctgtagaacacctttcctatggagtct (SEQ ID NO: 150)

TABLE 3-continued

DNA C-FISH Pre-decoding Probes

5'→3'

5'-tcatccgatatggtgatccatttttttccacggcaccctcctaccaaggctcttgca (SEQ ID NO: 151)

5'-tcatccgatatggtgatccatttttggcagcagcttagaaggccaagacttagctgc (SEQ ID NO: 152)

5'-tcatccgatatggtgatccatttttcttgcagtagtcaagcatgacataccctattt (SEQ ID NO: 153)

5'-tcatccgatatggtgatccatttttagctgtccatgaatttggaagtgatgtccctg (SEQ ID NO: 154)

5'-tcatccgatatggtgatccatttttaagtaccatggatgtgtataggctcctgagtc (SEQ ID NO: 155)

5'-tcatccgatatggtgatccatttttctccttccctctggcacataggtatgttcca (SEQ ID NO: 156)

5'-tcatccgatatggtgatccatttttaatagtgacccaacgagatctcctgtgaaatg (SEQ ID NO: 157)

5'-tcatccgatatggtgatccatttttagaccaggagagttaattaattacctgaggac (SEQ ID NO: 158)

5'-tcatccgatatggtgatccatttttgtatacttctggccttctcaggagtaagcaga (SEQ ID NO: 159)

5'-tcatccgatatggtgatccatttttaccctcgatgaggaggtttggaaagaatggat (SEQ ID NO: 160)

5'-tcatccgatatggtgatccatttttgttgactctgtacttaatgtcagaagtggtgg (SEQ ID NO: 161)

5'-tcatccgatatggtgatccatttttcaaagataccacctgtcatgcaacatatatgt (SEQ ID NO: 162)

5'-tcatccgatatggtgatccatttttactgtcgtgatgtggaactccaaaaggtgaat (SEQ ID NO: 163)

5'-tcatccgatatggtgatccatttttatgcagaatgtcatcccttccatacttggcag (SEQ ID NO: 164)

5'-tcatccgatatggtgatccattttttgatttcgttaccttgaaccagtggccaaag (SEQ ID NO: 165)

5'-tcatccgatatggtgatccattttttgacatttgtgctttaggaccatactaggat (SEQ ID NO: 166)

5'-tcatccgatatggtgatccatttttcattaaacatgagcccttaaagcagcagttgc (SEQ ID NO: 167)

5'-tcatccgatatggtgatccatttttgagcaggttatctttattggcacaaatgttac (SEQ ID NO: 168)

5'-tcatccgatatggtgatccatttttgttgctctaggagaactggagtcctagcccag (SEQ ID NO: 169)

5'-tcatccgatatggtgatccatttttacaggccaaggagttgtgacccattagctttg (SEQ ID NO: 170)

5'-tcatccgatatggtgatccatttttgtgcatggctaagtcattagcttaaccattgc (SEQ ID NO: 171)

5'-tcatccgatatggtgatccatttttgagttcccagcagcaaccacagggagggccag (SEQ ID NO: 172)

5'-tcatccgatatggtgatccattttttgtcgcatgaacatgccacatctgtccacca (SEQ ID NO: 173)

5'-tcatccgatatggtgatccattttttgagaattgtcttcccagaagggtaggtcctt (SEQ ID NO: 174)

TABLE 4

DNA C-FISH Decoding Probes

| | | SEQ ID NO: |
|---|---|---|
| cycle1 | 5'-Quasar 570-tggatcaccatatcggatgattttttggctatgtccgtaacactccttttttggctatgtccgtaacactcc | 175 |
| cycle2 | 5'-Cy5-gaaccatggtacctgagatcgaaccatggtacctgagatcggagtgttacggacatagcc | 176 |
| cycle3 | 5'-Quasar 570-gatctcaggtaccatggttccgtccagattatgtttctcccgtccagattatgtttctcc | 177 |
| cycle4 | 5'-Cy5-cagcttagaatagaacattgcagcttagaatagaacattgggagaaacataatctggacg | 178 |
| cycle5 | 5'-Quasar 570-caatgttctattctaagctgttttttctggatgatgttctctcatcttttttctggatgatgttctctcatc | 179 |
| cycle6 | 5'-Cy5-gctcaagtgttggtgaagggctcaagtgttggtgaagggatgagagaacatcatccag | 180 |
| cycle7 | 5'-Quasar 570-accttcaccaacacttgagcttttttatagccctggacatgaacgtttttttatagccctggacatgaacgt | 181 |

TABLE 4-continued

DNA C-FISH Decoding Probes

| | | SEQ ID NO: |
|---|---|---|
| cycle8 | 5'-Cy5-cgtacagaggtagcaagggattttttcgtacagaggtagcaagggattttttacgttcatgtccagggctat | 182 |
| cycle9 | 5'-Quasar 570-tcccttgctacctctgtacgttttttcgatgcatcaggtacccagttttttcgatgcatcaggtacccagt | 183 |

TABLE 5

RNA C-FISH Decoding Probes

| | | SEQ ID NO: |
|---|---|---|
| GAPDH | | |
| cycle1 | 5'-Quasar 570-tggatcaccatatcggatgattttttggctatgtccgtaacactccttttttggctatgtccgtaacactcc | 184 |
| cycle2 | 5'-Cy5-gaaccatggtacctgagatcgaaccatggtacctgagatcggagtgttacggacatagcc | 185 |
| cycle3 | 5'-Quasar 570-gatctcaggtaccatggttccgtccagattatgtttctcccgtccagattatgtttctcc | 186 |
| cycle4 | 5'-Cy5-cagcttagaatagaacattgcagcttagaatagaacattgggagaaacataatctggacg | 187 |
| cycle5 | 5'-Quasar 570-caatgttctattctaagctgctggatgatgttctctcatcctggatgatgttctctcatc | 188 |
| cycle6 | 5'-Cy5-gctcaagtgttggtgaaggttttttgctcaagtgttggtgaagggatgagagaacatcatccag | 189 |
| cycle7 | 5'-Quasar 570-accttcaccaacacttgagcttttttatagccctggacatgaacgttttttatagccctggacatgaacgt | 190 |
| cycle8 | 5'-Cy5-cgtacagaggtagcaagggattttttcgtacagaggtagcaagggattttttacgttcatgtccagggctat | 191 |
| cycle9 | 5'-Quasar 570-tcccttgctacctctgtacgttttttcgatgcatcaggtacccagttttttcgatgcatcaggtacccagt | 192 |
| Cycle10 | 5'-Cy5-gatggtcgtagtgtggcacagatggtcgtagtgtggcacattttttactgggtacctgatgcatcg | 193 |
| Cycle11 | 5'-Quasar 570-tgtgccacactacgaccatcttttttatgagtcttccagtcgtagtttttttatgagtcttccagtcgtagt | 194 |
| Cycle12 | 5'-Cy5-tcacgtaatgttctccacgacacgtaatgttctccacgattttttactacgactggaagactcat | 195 |
| Cycle13 | 5'-Quasar 570-tcgtggagaacattacgtgattttttcttgctatcttccagcgaagttttttcttgctatcttccagcgaag | 196 |
| Cycle14 | 5'-Cy5-tagttgaaggagtgctcgtgagttgaaggagtgctcgtgcttcgctggaagatagcaag | 197 |
| Cycle15 | 5'-Quasar 570-cacgagcactccttcaactattttttcacttcgtcatggagcatgattttttcacttcgtcatggagcatga | 198 |
| Cycle16 | 5'-Cy5-tcatgctccatgacgaagtg | 199 |
| Ki67 | | |
| Cycle1 | 5'-Cy5-ccgcagacatctgtaaagacccgatgttgacggactaatcccgatgttgacggactaatc | 200 |
| Cycle2 | 5'-Quasar 570-tagtagttcagacgccgttattttttagtagttcagacgccgttattttttgattagtccgtcaacatcgg | 201 |
| Cycle3 | 5'-Cy5-taacggcgtctgaactactaccgtacctagatacactcaaccgtacctagatacactcaa | 202 |
| Cycle4 | 5'-Quasar 570-ccaggcaatatggtggtacattttttccaggcaatatggtggtacattttttttgagtgtatctaggtacgg | 203 |
| Cycle5 | 5'-Cy5-tgtaccaccatattgcctggttttttcgtgaagcttgagtggaatcttttttcgtgaagcttgagtggaatc | 204 |
| Cycle6 | 5'-Quasar 570-gtgtgaggcgctagagcatattttttgtgtgaggcgctagagcatattttttgattccactcaagcttcacg | 205 |
| Cycle7 | 5'-Cy5-tatgctctagcgcctcacacggtatggcacgcctaatctgggtatggcacgcctaatctg | 206 |

TABLE 5-continued

RNA C-FISH Decoding Probes

| | | SEQ ID NO: |
|---|---|---|
| Cycle8 | 5'-Quasar 570-atctccagtggcatccttcttttttatctccagtggcatccttcttttttcagattaggcgtgccatacc | 207 |
| Cycle9 | 5'-Cy5-agaaggatgccactggagaggtaactgcgcatagttggcggtaactgcgcatagttggc | 208 |
| Cycle10 | 5'-Quasar 570-ggtacagtaagtgagaatccttttttggtacagtaagtgagaatccttttttgccaactatgcgcagttacc | 209 |
| Cycle11 | 5'-Cy5-ggattctcacttactgtaccgccaccttaacacgcgatgagccaccttaacacgcgatga | 210 |
| Cycle12 | 5'-Quasar 570-cattgatcttggtgctgctgttttttcattgatcttggtgctgctgttttttcatcgcgtgttaaggtggc | 211 |
| Cycle13 | 5'-Cy5-cagcagcaccaagatcaatggctattacgagcgcttggagctattacgagcgcttggat | 212 |
| Cycle14 | 5'-Quasar 570-tatgttgtgccttacgcctcttttttatgttgtgccttacgcctcatccaagcgctcgtaatagc | 213 |
| Cycle15 | 5'-Cy5-gaggcgtaaggcacaacatattttttttaaccgaactgacggccaaaccgaactgacggccat | 214 |
| Cycle16 | 5'-Quasar 570-atggccgtcagttcggttaa | 215 |

Example 3: Production of C-FISH Probes

Figure 5:
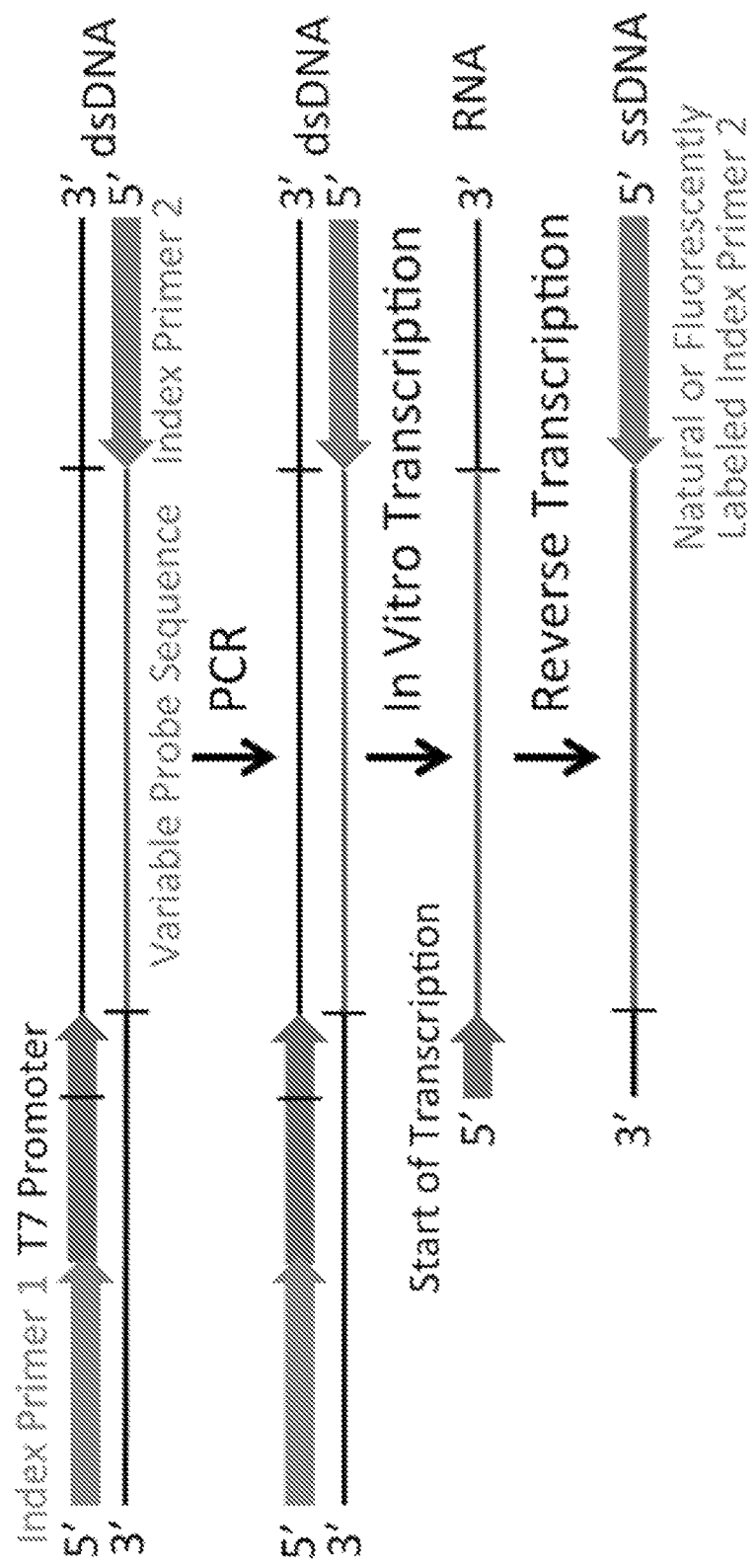
FIG. 5 is a schematic illustrating an exemplary protocol for preparing C-FISH probes by enzymatic amplification of an array-derived oligonucleotide pool. Each sequence in the oligonucleotide pool contains a T7 promoter sequence, a variable probe sequence, and two flanking index primers. First, templates from a library of probes are selected and amplified by indexed PCR (polymerase chain reaction). Next, the resulting PCR products are further amplified into RNA by in vitro transcription. Finally, the RNA library is reverse transcribed into cDNA. Natural (unlabeled) or fluorescently labeled oligonucleotides are used as reverse transcription to generate pre-decoding or decoding probes, respectively.

As shown in FIG. 5, C-FISH probes can be obtained by enzymatic amplification of an array-derived oligonucleotide pool. Each sequence in the oligonucleotide pool contains a T7 promoter sequence, a variable probe sequence, and two flanking index primers. First, templates from a library of probes are selected and amplified by indexed PCR (polymerase chain reaction). Next, the resulting PCR products are further amplified into RNA by in vitro transcription. Finally, the RNA library is reverse transcribed into cDNA. Natural (unlabeled) or fluorescently labeled oligonucleotides are used as reverse transcription to generate pre-decoding or decoding probes, respectively.

Using the protocol illustrated in FIG. 5, RNA C-FISH probes are designed and generated for 30 selected genes in mTOR, PI(3)K, Ras, Wnt, or Notch pathways, as the transcriptional profiles of these genes in HeLa cells are well documented by RNA-Seq. To make C-FISH signals detectable, at least 40 pre-decoding probes are required to hybridize to individual transcripts. To cost-effectively generate these large number of predecoding probes simultaneously, a well-established oligopaint protocol is used (see FIG. 5). This protocol has been successfully applied in our laboratory to prepare libraries of oligonucleotides for in situ DNA analysis.

Briefly, PCR reactions are performed to amplify the 1200 probe sequences from a library of array-derived oligonucleotides containing tens of thousands of custom sequences. After purification using a Zymo DNA purification column, the PCR products are further amplified by transcription into RNA using a T7 in vitro transcription kit. The T7 reaction is incubated at 37° C. for 4 hours to maximize yield. Subsequently, the RNA products are purified using a RNeasy spin column and reverse-transcribed into single-stranded pre-coding probes using Maxima reverse transcription kit. To selectively hydrolyze the template RNA, 20 μL of 0.25 M EDTA and 0.5 N NaOH are added to 50 μL of the reaction mixture. After incubation at 95° C. for 10 minutes, the library of the pre-coding probes is then purified using a Zymo DNA purification column. To analyze 30 different transcripts with decoding probes labeled with two different fluorophores, 5 cycles of C-FISH ($2^5$=32) and 150 (30×5) orthogonal decoding probes are required. A DNA synthesizer is used to prepare this relatively small number of amino modified oligonucleotides. For each cycle of C-FISH, 15 decoding probes are labeled with Quasar 570 and another 15 decoding probes are labeled with Cy5. To couple the 15 probes to corresponding fluorophores simultaneously, a reaction mixture is prepared that contains 1 nmol of combined oligonucleotides, 100 nmol NHS ester modified fluorophores, 1 nL of 1 M NaHCO$_3$ and 9 nL of nuclease free water. After incubation at room temperature overnight, the generated fluorescent decoding probes are purified using an HPLC equipped with a C18 column.

Figure 6:
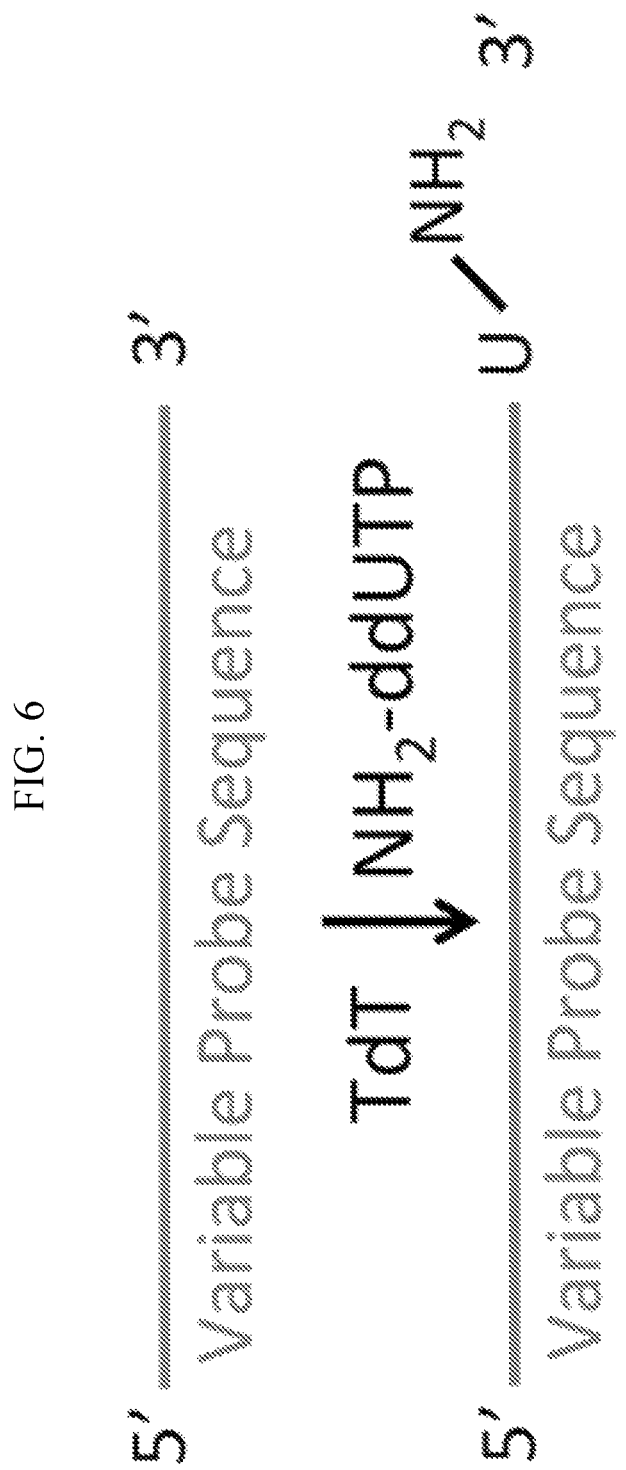
FIG. 6 is a schematic illustrating an exemplary protocol for preparing C-FISH decoding probes by chemical synthesis followed by enzymatic incorporation. Generated on a DNA synthesizer, decoding probes comprising unlabeled nucleotides are extended with $NH_2$-ddUTP (2',3'-dideoxyuridine-5'-triphosphate) by terminal transferase (TdT), which is a template independent polymerase that catalyzes the addition of deoxynucleotides to the 3' hydroxyl terminus of DNA molecules.

As shown in FIG. 6, C-FISH decoding probes can be obtained by chemical synthesis followed by enzymatic incorporation. Generated on a DNA synthesizer, decoding probes comprising unlabeled nucleotides are extended with NH$_2$-ddUTP (2',3'-dideoxyuridine-5'-triphosphate) by terminal transferase (TdT), which is a template independent polymerase that catalyzes the addition of deoxynucleotides to the 3' hydroxyl terminus of DNA molecules.

Using such a protocol, RNA C-FISH probes are designed and generated for 100 selected genes in mTOR, PI(3)K, Ras, Wnt, or Notch pathways using well documented transcriptional profiles in HeLa cells[16]. The large number (100×40=4,000) of pre-decoding C-FISH probes for these 100 transcripts are prepared using the chemical synthesis followed by enzymatic incorporation approach as discussed above. To quantify 100 different transcripts using decoding probes labeled with two different fluorophores, 7 cycles of C-FISH ($2^7$=128) and 700 (100×7) orthogonal decoding probes will be required. To generate these decoding probes precisely and cost-effectively, a DNA synthesizer is used first to prepare all 700 decoding probes with natural, unlabeled nucleotides. Subsequently, each of the 50 probes that will be used in the same C-FISH cycle are combined and labeled with the same fluorophore. Then, a template-independent terminal transferase (TdT) is used to incorporate amino modified ddUTP at the 3' ends of all 50 probes simultaneously (see FIG. 6). To 1 mL of 1× TdT reaction buffer, 100 μL of 2.5 mM CoCl$_2$, 1 nmol of combined oligonucleotides, 5 nmol amino modified ddUTP, and 1 unit of TdT are added. After incubated at 37° C. for 1 hour, the extended oligonucleotides are purified using a Qiagen nucleotide removal column. Finally, the amino modified decoding probes are coupled the specific fluorophores and purified by HPLC, using the same protocol as described above. The decoding probes will be precisely generated using this approach, as they are prepared one by one on a DNA synthesizer. Additionally, since 3' amino modifier phosphoramidite ($8/25 nmol) is much more expensive than natural nucleotides ($0.1/25 nmol), we will dramatically reduce the probe preparation cost by avoiding the direct chemical synthesis of amino modified probes.

Example 4: C-FISH Probes Labeled with Cleavable Fluorophores

Figure 7:
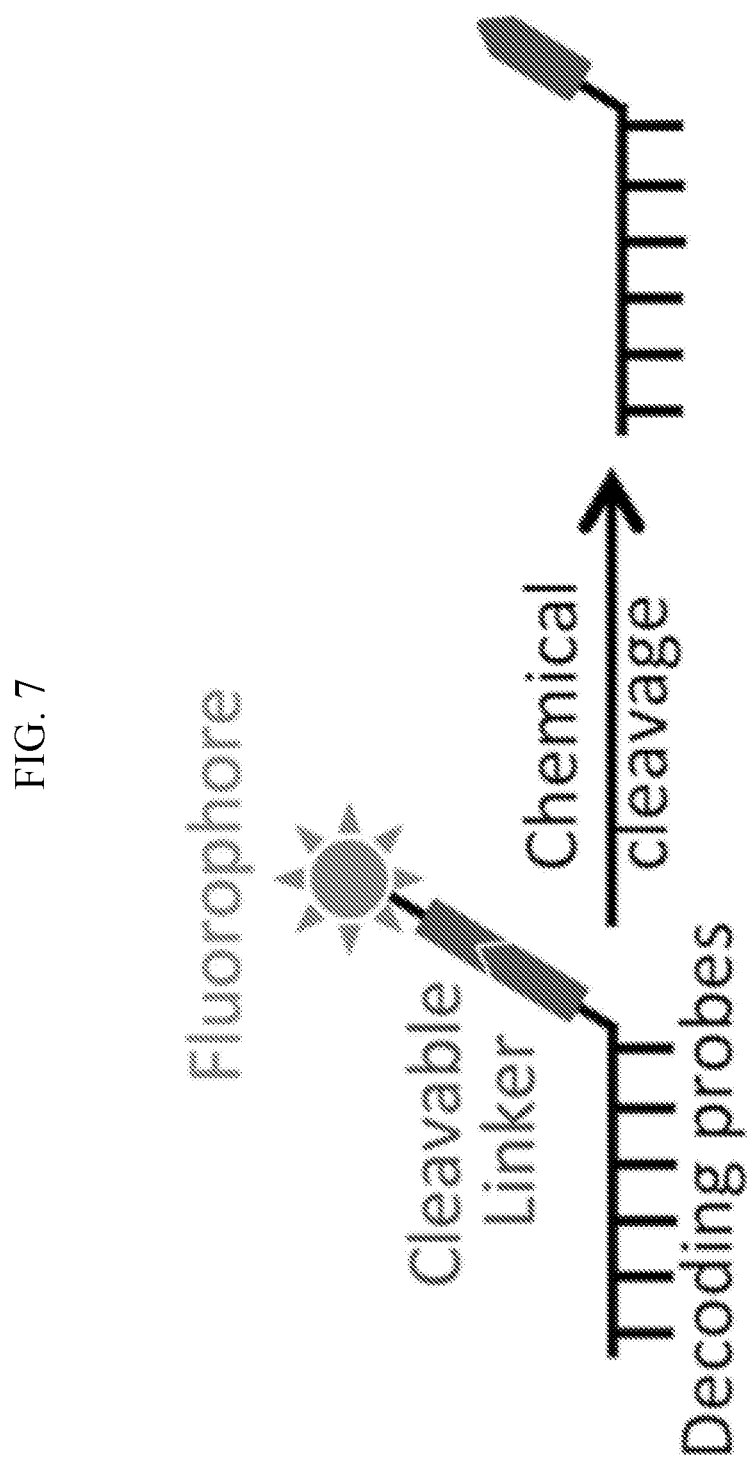
FIG. 7 illustrates chemical cleavage of fluorescent decoding probes for high-throughput and rapid C-FISH.

As shown in FIG. 7, fluorophores are attached to the oligonucleotides through a chemically cleavable linker. After hybridization with these probes, it is possible to simultaneously chemically cleave all of the different fluorophores in the whole sample in a short time.

Figures 8A, 8B, 8C, 8D:
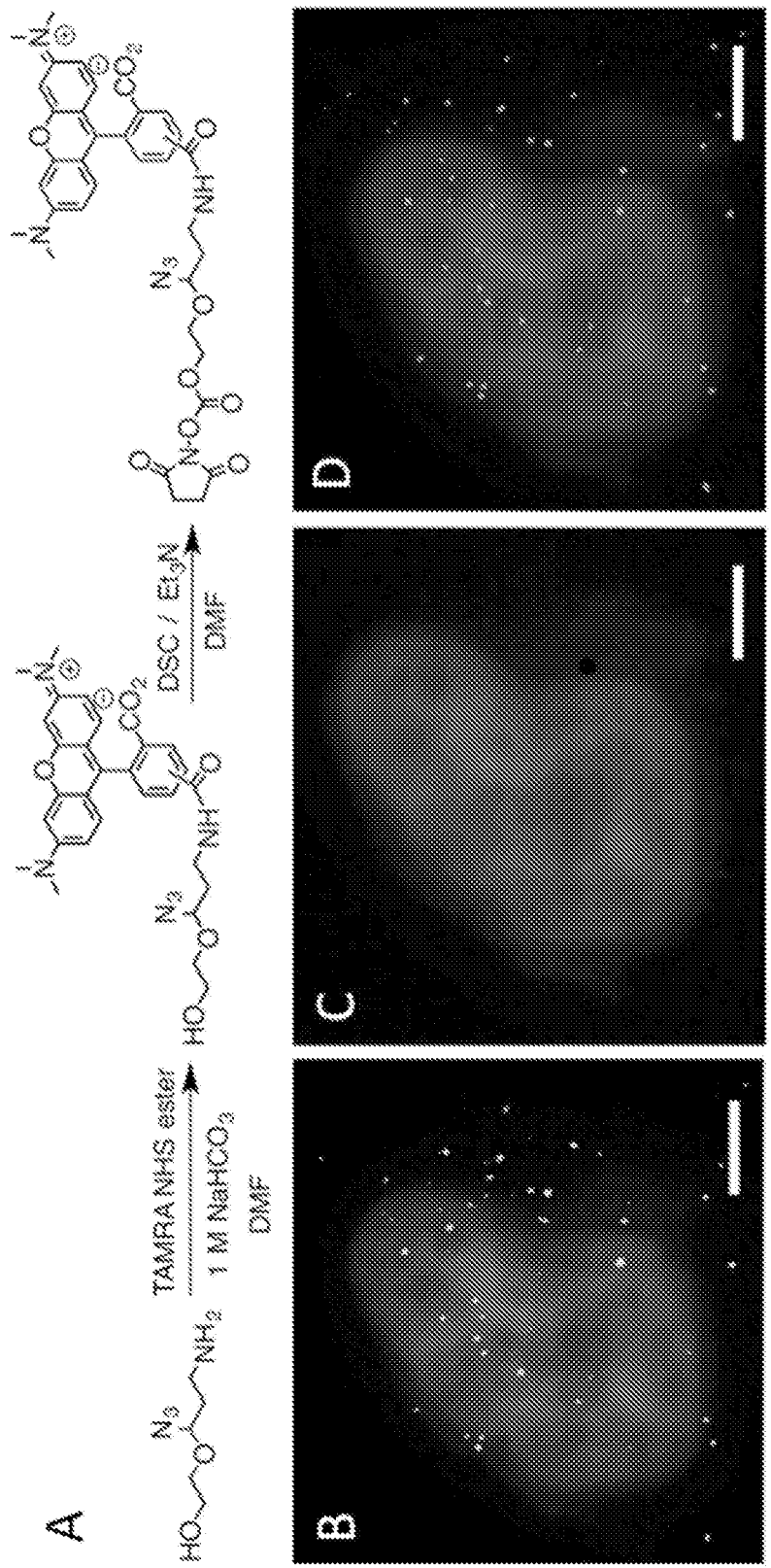
FIGS. 8A-8D. (A) Synthesis of NHS ester functionalized cleavable TAMRA. (B) Ki67 transcripts are detected by cleavable TAMRA labeled decoding probes. (C) Fluorescence signals are removed by chemical cleavage using TCEP. (D) Ki67 transcripts reappear after the second cycle of hybridization with Cy5 labeled decoding probes. Scale bars, 5 μm.

To assess the feasibility of this approach, we designed and synthesized an azido-based linker (FIG. 8A). The amino group on one end of the linker was coupled with TAMRA NHS ester. Then, the hydroxyl group on the other end of the linker was converted into a new NHS ester group. This group was used to conjugate cleavable TAMRA to amino groups on oligonucleotides. Using this scheme, we can prepared cleavable fluorescent C-FISH probes labeled with any commercially available NHS fluorophores. With the cleavable TAMRA labeled probes, we performed C-FISH to analyze Ki67 transcripts. After the first cycle of hybridization and imaging (FIG. 8B), the cells were incubated with 100 mM tris(2-carboxyethyl)phosphine (TCEP) at 37° C. and pH 9.0 for 30 minutes. With the cleavage efficiency of more than 95%, this chemical cleavage reaction erased all the original fluorescent spots (FIG. 8C). After the second cycle of hybridization with Cy5 labeled probes, almost all the spots reappear (FIG. 8D), suggesting that the TCEP treatment does not damage RNA molecules. The very small number of non-colocalized spots may be generated by non-specific probe binding. Additionally, the color of all the spots were determined accurately, indicating the minimum leftover signals from the previous cycle does not interfere with the subsequent cycles. The copy numbers and spatial distributions of Ki67 transcripts obtained by cleavable C-FISH probes are consistent with those in conventional smFISH (FIG. 2C). These results demonstrate that the fluorophores on cleavable fluorescent C-FISH probes can be efficiently removed by a RNA compatible reaction within 30 minutes, which enables high-throughput and rapid RNA analysis in single cells in situ.

Example 5—Two-Probe C-FISH Method

In first-generation C-FISH, each transcript or genomic locus requires a unique decoding probe per hybridization cycle. For in situ genome or transcriptome analysis, a large number of decoding probes must be designed and prepared. As a result, the potential cross-hybridization between these decoding probes may lead to false positive signals. Additionally, the cost to prepare this large number of probes can be relatively high.

To further minimize the possibility of probe cross-hybridization and reduce the assay cost, we developed the second-generation C-FISH with only two decoding probes for each transcript or genomic locus. In this approach, each transcript or genomic locus is hybridized with a set of pre-decoding probes. These probes have varied targeting sequences to bind to the different regions on the target, and the shared decoding sequence to bind to decoding probes. Subsequently, the fluorescently labeled decoding probe "A" hybridizes to the pre-decoding probes, and also introduces the binding sites for the probe used in the second cycle. After fluorescence imaging and data storage, the fluorescence signals are efficiently removed. Then, the fluorescently labeled decoding probe "B" hybridizes to the decoding probe "A", and also introduces the binding sites, which will be hybridized by decoding probe "A" again in the third hybridization cycle. Through consecutive hybridization of probes "A" and "B", each transcript or genomic loci is identified as a fluorescent spot with a unique color sequence. In this way, to quantify 30,000 transcripts or genomic loci with two colors, the number of required decoding probes is reduced about one order of magnitude from 480,000 to 60,000.

Figure 9:
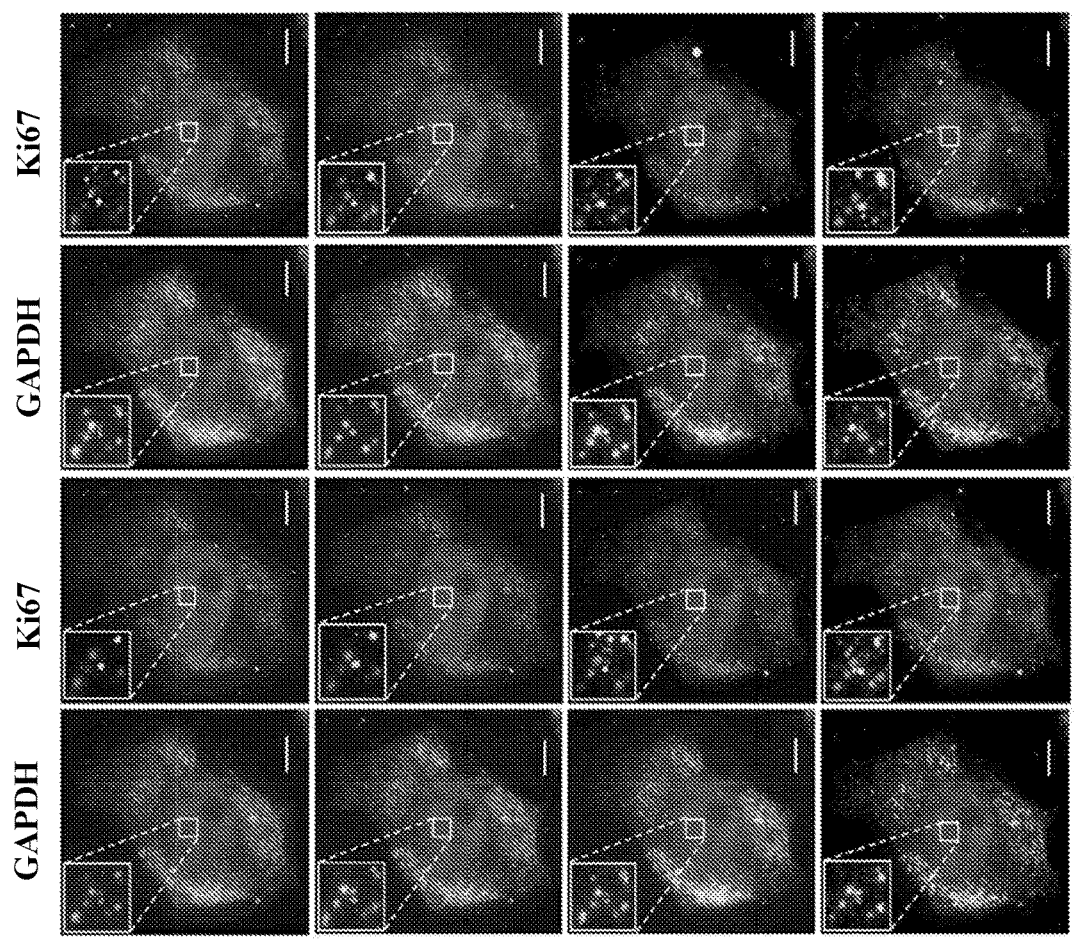
FIG. 9. Single-cell in situ transcripts analysis by the second-generation C-FISH. In the first cycle of C-FISH, GAPDH and Ki67 transcripts were detected as green and red spots, respectively. Through 16 cycles of C-FISH using only two decoding probes for each transcript, individual transcripts are detected as fluorescent spots with unique color sequences. Scale bars, 5 μm.

To demonstrate the feasibility of this approach, we stained two mRNA GAPDH and Ki67 with only 4 decoding probes by 16 cycles of consecutive hybridization. As shown in FIG. 9, each individual transcript is unambiguously detected. The results obtained by the second-generation C-FISH and the first-generation C-FISH closely resemble each other. These results suggest that transcripts and genomic loci can be quantitatively detected in single cells in situ by the second-generation C-FISH.

The experimental methods for the first-generation and second-generation C-FISH are similar. The predecoding probes used in the two approaches are the same. The sequences of the decoding probes used in the second-generation C-FISH are as follows:

```
GAPDH

Probe "A"    5'-Quasar 570-
             tggatcaccatatcggatgattttttggctatgtccgtaacactccttttttggctatgtccgtaacactcc
             (SEQ ID NO: 216)

Probe "B"    5'-Cy5-tcatccgatatggtgatccacatccgatatggtgatccaggagtgttacggacatagcc
             (SEQ ID NO: 217)

Ki67

Probe "A"    5'-Cy5-ccgcagacatctgtaaagacttttttccgatgttgacggactaatcttttttccgatgttgacggactaatc
             (SEQ ID NO: 218)

Probe "B"    5'-Quasar 570-
             gtctttacagatgtctgcggtttttgtctttacagatgtctgcggttttttgattagtccgtcaacatcgg
             (SEQ ID NO: 219)
```

The present invention has been described in terms of one or more preferred embodiments, and it should be appreciated that many equivalents, alternatives, variations, and modifications, aside from those expressly stated, are possible and within the scope of the invention.

I claim:

1. A method of detecting transcripts or genomic loci in situ in a single cell, the method comprising the following steps:

(a) performing a first contacting step that comprises contacting a single cell comprising a plurality of transcripts or genomic loci to a plurality of pre-decoding oligonucleotides, wherein the pre-decoding oligonucleotides are unlabeled, wherein each of the plurality of pre-decoding oligonucleotides comprises a targeting sequence that specifically hybridizes to one target transcript or genomic locus of the plurality of transcripts or genomic loci and further comprises one or more binding sites that specifically hybridize to one of a plurality of decoding oligonucleotides in a subsequent hybridization step, and wherein the first contacting step occurs under conditions that promote hybridization of the plurality of pre-decoding oligonucleotides to the plurality of transcripts or genomic loci;

(b) after step (a), washing the cell to remove the pre-decoding oligonucleotides that are not hybridized or are non-specifically hybridized to the transcripts or genomic loci in the cell;

(c) after step (b), performing a second contacting step that comprises contacting the cell with the plurality of decoding oligonucleotides; wherein each of the plurality of decoding oligonucleotides comprises a different detectable moiety capable of generating a different signal, a binding site that specifically hybridizes to one of plurality of the pre-decoding oligonucleotides, and two or more binding sites that specifically hybridize to one of an another plurality of decoding oligonucleotides; and wherein the second contacting step occurs under conditions that promote hybridization of the plurality of decoding oligonucleotides to the plurality of pre-decoding oligonucleotides;

(d) after step (c), washing the cell to remove the plurality of decoding oligonucleotides that are not hybridized or are non-specifically hybridized to the plurality of pre-decoding oligonucleotides in the cell, (g) after step (d), imaging the cell by detecting a plurality of different detectable signals generated from the different detectable moiety of each of the plurality of decoding oligonucleotides hybridized to the pre-decoding oligonucleotides, wherein detection of the plurality of different detectable signals in the cell indicates the presence of the plurality of target transcripts or genomic loci in the cell:

(f) after step (e), removing the different detectable moiety from each of the plurality of decoding oligonucleotides that are specifically hybridized to the plurality of pre-decoding oligonucleotides in the cell and maintaining the hybridization between the plurality of decoding oligonucleotides and the plurality of pre-decoding oligonucleotides in the cell;

(g) repeating steps (c) to (f), wherein the another plurality of detectably labeled decoding oligonucleotides is used in step (c) of step (g) to replace the plurality of decoding oligonucleotides and hybridize to the plurality of decoding oligonucleotides, and wherein the detectable moiety of each of the another plurality of detectably labeled decoding oligonucleotides comprises a different detectable moiety capable of generating a different signal.

2. The method of claim 1, wherein steps (c)-(f) are consecutively performed at least 16 times.

3. The method of claim 1, further comprises performing steps c) to f) for two or more cycles, wherein each of the another plurality of decoding oligonucleotides used in a previous cycle of the two or more cycles has two or more binding sites that specifically hybridize to one of the another plurality of decoding oligonucleotides used in a following later cycle of the two or more cycles and the another plurality of decoding oligonucleotides used in the previous cycle of the two or more cycles hybridizes to the another plurality of decoding oligonucleotides used in the following later cycle of the two or more cycles in step (c), and wherein the plurality of decoding oligonucleotides are two decoding oligonucleotides.

4. The method of claim 1, wherein the detectable moiety is selected from the group consisting of a fluorophore, a radioactive isotope, and a metal isotope.

5. The method of claim 4, wherein the fluorophore is TAMRA ATTO G47N, and ATTO 700.

6. The method of claim 1, wherein the plurality of pre-decoding oligonucleotides hybridizes to at least 10 different transcripts or genomic loci from the plurality of transcripts or genomic loci.

7. The method of claim 1, wherein the detectable moiety in step (f) is removed by a chemical cleavage.

* * * * *

UNITED STATES PATENT AND TRADEMARK OFFICE
CERTIFICATE OF CORRECTION

PATENT NO. : 11,512,344 B2
APPLICATION NO. : 16/300148
DATED : November 29, 2022
INVENTOR(S) : Jia Guo It is certified that error appears in the above-identified patent and that said Letters Patent is hereby corrected as shown below:

In the Claims

Claim 1, Column 103, Line 33, "(g)" should read --(e)--.

Signed and Sealed this
Twenty-second Day of August, 2023

Katherine Kelly Vidal
*Director of the United States Patent and Trademark Office*